US012625106B2

(12) United States Patent
Zhao et al.

(10) Patent No.: US 12,625,106 B2
(45) Date of Patent: May 12, 2026

(54) DETECTION BASE BOARD AND DETECTION CHIP

(71) Applicants:Beijing BOE Technology Development Co., Ltd., Beijing (CN); BOE Technology Group Co., Ltd., Beijing (CN)

(72) Inventors: Zijian Zhao, Beijing (CN); Shinying Lau, Beijing (CN); Yaqi Zhang, Beijing (CN)

(73) Assignees: BEIJING BOE TECHNOLOGY DEVELOPMENT CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 198 days.

(21) Appl. No.: 18/692,100

(22) PCT Filed: Aug. 31, 2023

(86) PCT No.: PCT/CN2023/116170
§ 371 (c)(1),
(2) Date: Mar. 14, 2024

(87) PCT Pub. No.: WO2025/043618
PCT Pub. Date: Mar. 6, 2025

(65) Prior Publication Data
US 2025/0231139 A1 Jul. 17, 2025

(51) Int. Cl.
*G01N 27/414* (2006.01)
*G01N 27/12* (2006.01)
*G01N 33/543* (2006.01)

(52) U.S. Cl.
CPC ......... *G01N 27/4145* (2013.01); *G01N 27/12* (2013.01); *G01N 33/5438* (2013.01)

(58) Field of Classification Search
CPC .. G01N 27/4145; G01N 27/12; G01N 27/327; G01N 27/3272; G01N 27/3276; G01N 33/5438; G01N 33/4836
See application file for complete search history.

(56) References Cited

U.S. PATENT DOCUMENTS 7,470,533 B2 * 12/2008 Xu ......................... C12M 41/36
435/288.2
11,125,716 B2 * 9/2021 Ogi ....................... G01N 27/27
(Continued)

FOREIGN PATENT DOCUMENTS

CN 105738456 A 7/2016
CN 205844251 U 12/2016
(Continued)

*Primary Examiner* — Alexander S Noguerola
(74) *Attorney, Agent, or Firm* — WHDA, LLP

(57) ABSTRACT

A detection base board and a detection chip, which relates to the technical field of biological detection. The detection base board includes a plurality of detecting units, each of the detecting units includes a sensing unit and a signal generating unit, and the sensing unit and the signal generating unit are electrically connected; the sensing unit is configured to react with a sample to be detected and generate an electric signal, and the signal generating unit is configured to receive the electric signal and generate a detection current; the sensing unit includes a pair of sensing electrodes, and the pair of sensing electrodes are electrically connected to the signal generating unit; and both of the outer contours of the sensing electrodes include an arc line. The detection base board is used for the fabrication of high-sensitivity and high-accuracy detection chips.

16 Claims, 7 Drawing Sheets

(56)            References Cited

U.S. PATENT DOCUMENTS

| | | |
|---|---|---|
| 2017/0067890 A1 | 3/2017 | Lin et al. |
| 2018/0095052 A1 | 4/2018 | Jun |
| 2020/0284753 A1 | 9/2020 | Ionescu et al. |
| 2021/0162409 A1 | 6/2021 | Yao et al. |
| 2021/0263022 A1 | 8/2021 | Huang et al. |

FOREIGN PATENT DOCUMENTS

| | | | |
|---|---|---|---|
| CN | 107703198 | A | 2/2018 |
| CN | 110168364 | A | 8/2019 |
| CN | 111175367 | A | 5/2020 |
| CN | 111521546 | A | 8/2020 |
| CN | 115791908 | A | 3/2023 |
| WO | 2021/100790 | A1 | 5/2021 |

* cited by examiner

DETECTION BASE BOARD AND DETECTION CHIP

TECHNICAL FIELD

The present application relates to the technical field of biological detection, and particularly relates to a detection base board and a detection chip.

BACKGROUND

Acute myelogenous leukemia (AML) is a commonly seen adult acute leukemia, and its morbidity increases year by year (1.62/10 ten thousands). AML has a high heterogeneity, and currently there has not been an effective method of early detection.

Complete blood cell count and peripheral blood smear are the most commonly seen AML lookup methods. In the blood of most of the AML patients there are many immature leukocytes, while the erythrocytes or the thrombocytes are insufficient. However, those discoveries merely might serve as prompting, and cannot be used as the basis for definite diagnosis, and the definite diagnosis requires the combination with bone marrow biopsy, which causes pain of the patient. Therefore, a non-invasive, quick, high-sensitivity detecting method is currently a research hotspot in AML early diagnosis and prognosis.

SUMMARY

The embodiments of the present application employ the following technical solutions:

In the first aspect, an embodiment of the present application provides a detection base board, wherein the detection base board comprises a substrate;

the substrate comprises a sample testing region;

the sample testing region comprises a plurality of detecting units, each of the detecting units comprises a sensing unit and a signal generating unit, and the sensing unit and the signal generating unit are electrically connected;

the sensing unit is configured to react with a sample to be detected and generate an electric signal, and the signal generating unit is configured to receive the electric signal and generate a detection current;

the sensing unit comprises a pair of sensing electrodes, and the pair of sensing electrodes are electrically connected to the signal generating unit; and contours of the sensing electrodes comprise an are line.

In at least one embodiment of the present application, the signal generating unit comprises a bigrid transistor, and a first grid and a second grid of the bigrid transistor are configured to be connected to different electrically conducting components.

In at least one embodiment of the present application, the sensing unit further comprises an antibody located on the pair of sensing electrodes, and the antibody and the sensing electrodes are configured to be connected by covalent bonds;

types of the antibodies on the pairs of sensing electrodes are different; and the sensing unit further comprises a surface-treatment layer, the surface-treatment layer covers the pairs of sensing electrodes, and the surface-treatment layer is configured to form the covalent bonds with the antibodies.

In at least one embodiment of the present application, each of the sensing electrodes comprises a plurality of extending parts and a connecting part connecting the extending parts;

in a same sensing electrode, and the connecting part is located on a same side of the extending parts; and the sensing unit comprises a first sensing electrode and a second sensing electrode, a pattern of an orthographic projection on the substrate of the connecting part of the first sensing electrode and two extending parts connected to two ends of the connecting part is a first arch, a pattern of an orthographic projection on the substrate of the connecting part of the second sensing electrode and two extending parts connected to two ends of the connecting part is a second arch, and two ends of the first arch extend into a region enclosed by the second arch.

In at least one embodiment of the present application, a quantity of the extending parts of the first sensing electrode is at least two, a quantity of the extending parts of the second sensing electrode is at least three, and the extending parts of the first sensing electrode and the extending parts of the second sensing electrode are alternately arranged; and a shape of a pattern of an orthographic projection of each of the connecting parts on the substrate comprises an arc shape.

In at least one embodiment of the present application, a shape of a pattern of an orthographic projection of the first sensing electrode on the substrate is a U shape; and a shape of a pattern of an orthographic projection on the substrate of the connecting part of the second sensing electrode is an arc shape, and a shape of a pattern of an orthographic projection on the substrate of each of the extending parts of the second sensing electrode is a rectangle.

In at least one embodiment of the present application, the first grid of the bigrid transistor is electrically connected to a constant-voltage-signal inputting terminal, and the first grid is configured to control turning-on and turning-off of the bigrid transistor; and the second grid of the bigrid transistor is electrically connected to the pair of sensing electrodes, and the second grid is configured to control variation of an electric current in the bigrid transistor and simultaneously generating the detection current according to electric signals generated in the sensing electrodes.

In at least one embodiment of the present application, the substrate further comprises a signal-detection region located on at least one side of the sample-detection region, and the signal-detection region comprises at least one negative electrode terminal; and the negative electrode terminal is electrically connected to the second grid by the sensing electrodes.

In at least one embodiment of the present application, the negative electrode terminal is electrically connected to a correcting line, and the negative electrode terminal is configured to release electric charges inside the bigrid transistor to correct the bigrid transistor.

In at least one embodiment of the present application, the signal-detection region comprises a plurality of first signal acquiring terminals, the first signal acquiring terminals are electrically connected to the signal generating units, and a quantity of the first signal acquiring terminals is equal to a quantity of the signal generating units;

the signal-detection region further comprises a plurality of second signal acquiring terminals; and in each of the detecting units, a drain of the bigrid transistor is electrically connected to the first signal acquiring terminal, a source of the bigrid transistor is electrically connected to the second signal acquiring terminal; the first signal acquiring terminal, the drain of the bigrid transistor, the source of the bigrid transistor and the second signal acquiring terminal are configured to form an electrically conducting loop, and the detection current refers to an electric current in the loop within a detection time period.

In at least one embodiment of the present application, the sample testing region comprises at least one reference unit, and the reference unit comprises a reference electrode and the bigrid transistor; and in the reference unit, the first grid of the bigrid transistor is electrically connected to the constant-voltage-signal inputting terminal, the first grid is configured to control the turning-on and turning-off of the bigrid transistor, the second grid of the bigrid transistor is electrically connected to the reference electrode, a drain of the bigrid transistor is electrically connected to the first signal acquiring terminal, and a source of the bigrid transistor is electrically connected to the second signal acquiring terminal.

In at least one embodiment of the present application, the sample testing region comprises a first sub-region and a second sub-region;

the substrate comprises a first signal-detection sub-region and a second signal-detection sub-region that are located on two sides of the sample testing region;

each of the first sub-region and the second sub-region comprises eight detecting units;

within the first sub-region, four detecting units are arranged in a first direction, and the other four detecting units are arranged in a second direction, wherein the first direction and the second direction intersect;

the first direction and a direction from the first sub-region pointing to the second sub-region form an acute angle therebetween, and the second direction and the direction from the first sub-region pointing to the second sub-region form an acute angle therebetween; and arrangement of the detecting units within the second sub-region and arrangement of the detecting units within the first sub-region are symmetrical.

In at least one embodiment of the present application, the first sub-region comprises one first trace, the second sub-region comprises one second trace, and the first trace and the second trace have equal lengths and are arranged symmetrically;

both of the first trace and the second trace extend in the direction from the first sub-region pointing to the second sub-region; and the first trace is configured to connect the eight detecting units within the first sub-region together in series, and the second trace is configured to connect the eight detecting units within the second sub-region together in series.

In at least one embodiment of the present application, the first signal-detection sub-region is located on one side of the first sub-region away from the second sub-region, and the second signal-detection sub-region is located on one side of the second sub-region away from the first sub-region; and the first signal-detection sub-region comprises a first negative electrode terminal, the second signal-detection sub-region comprises a second negative electrode terminal, all of the second grids of all of the bigrid transistors within the first sub-region are electrically connected to the first negative electrode terminal by sequentially the sensing electrodes and the first trace, and all of the second grids of all of the bigrid transistors within the second sub-region are electrically connected to the second negative electrode terminal by sequentially the sensing electrodes and the second trace.

In at least one embodiment of the present application, within the first sub-region or the second sub-region, in a direction parallel to a plane where the substrate is located, a minimum distance between any two neighboring sensing units is greater than or equal to 1.2 cm.

In at least one embodiment of the present application, the detection base board further comprises a plurality of third traces, and a direction of extension of the third traces intersects with the first trace;

some of the third traces are configured to connect the first trace and the detecting units within the first sub-region, and the other of the third traces are configured to connect the second trace and the detecting units within the second sub-region; and both of a range of lengths of traces connecting the detecting units and the first negative electrode terminal within the first sub-region and a range of lengths of traces connecting the detecting units and the second negative electrode terminal within the second sub-region are 0.5 cm-5 cm.

In at least one embodiment of the present application, the detection base board comprises a first electrically conducting layer, a first insulating layer, a semiconductor layer, a second insulating layer, a second electrically conducting layer, a third insulating layer, a source-drain electrically conducting layer, a fourth insulating layer and a third electrically conducting layer that are located on the substrate and are sequentially arranged;

the first electrically conducting layer comprises the first grids of the bigrid transistors, the semiconductor layer comprises active parts of the bigrid transistors, the second electrically conducting layer comprises the second grids of the bigrid transistors and a plurality of first connecting electrodes, and the source-drain electrically conducting layer comprises the sources and the drains of the bigrid transistors and a plurality of second connecting electrodes; and the sensing electrodes are electrically connected to the second grids of the bigrid transistors by sequentially the second connecting electrodes and the first connecting electrodes.

In the second aspect, an embodiment of the present application provides a detection chip, wherein the detection chip comprises the detection base board according to any one of the embodiments in the first aspect, and further comprises a cover plate and an adhesive layer, the cover plate covers the sample testing region of the detection base board, the cover plate is provided with a sample inputting hole and a sample outputting hole, the adhesive layer is located between the detection base board and the cover plate, and the detection base board, the cover plate and the adhesive layer form a cavity therebetween.

In at least one embodiment of the present application, all of the detecting units of the detection base board are located inside a same cavity.

The above description is merely a summary of the technical solutions of the present application. In order to more clearly know the elements of the present application to enable the implementation according to the contents of the description, and in order to make the above and other purposes, features and advantages of the present application more apparent and understandable, the particular embodiments of the present application are provided below.

BRIEF DESCRIPTION OF THE DRAWINGS

In order to more clearly illustrate the technical solutions of the embodiments of the present application or the related art, the figures that are required to describe the embodiments or the related art will be briefly described below. Apparently, the figures that are described below are merely embodiments of the present application, and a person skilled in the art can obtain other figures according to these figures without paying creative work.

DETAILED DESCRIPTION

Figure 1:
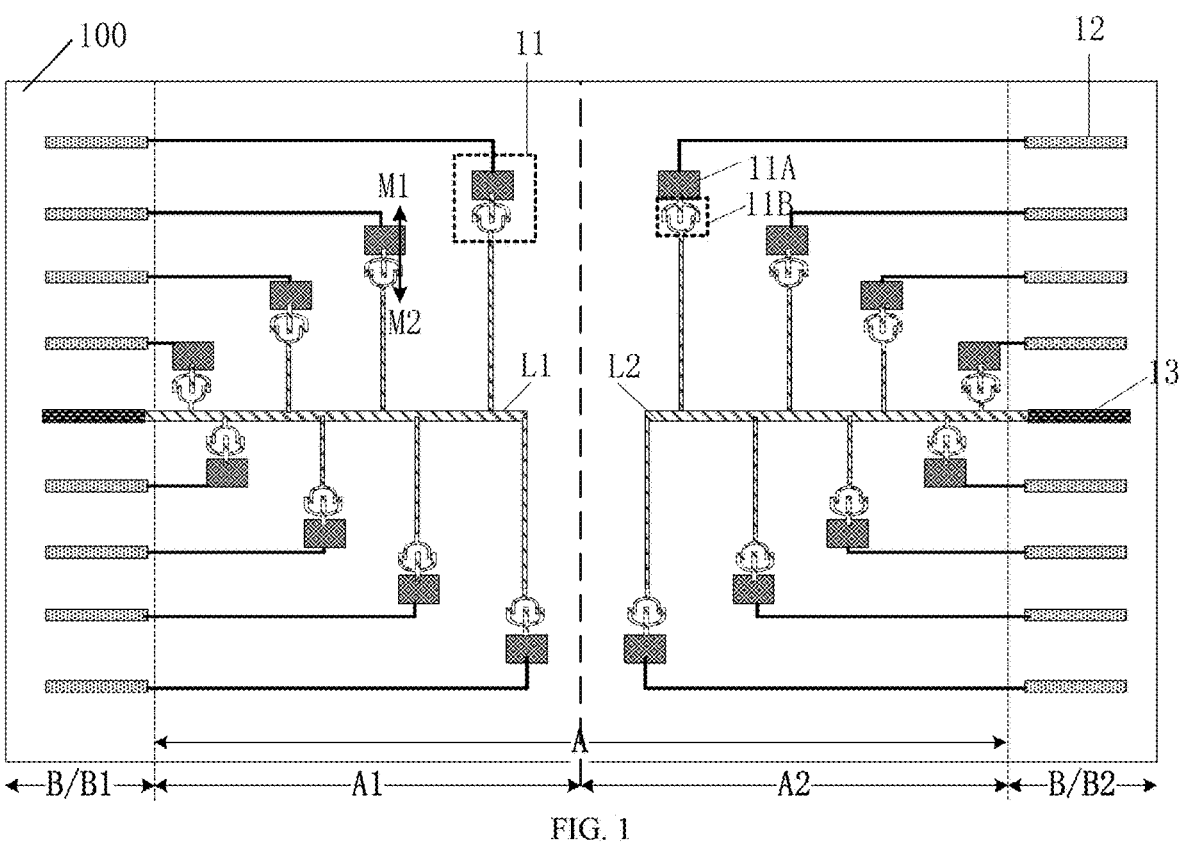
FIG. 1 is a schematic planar structural diagram of a detection base board according to an embodiment of the present application.

The technical solutions of the embodiments of the present application will be clearly and completely described below with reference to the drawings of the embodiments of the present application. Apparently, the described embodiments are merely certain embodiments of the present application, rather than all of the embodiments. All of the other embodiments that a person skilled in the art obtains on the basis of the embodiments of the present application without paying creative work fall within the protection scope of the present application.

In the embodiments of the present application, terms such as "first", "second", "third" and "fourth" are used to distinguish identical items or similar items that have substantially the same functions and effects, merely in order to clearly describe the technical solutions of the embodiments of the present application, and should not be construed as indicating or implying the degrees of importance or implicitly indicating the quantity of the specified technical features.

In the embodiments of the present application, the terms that indicate orientation or position relations, such as "upper" and "lower", are based on the orientation or position relations shown in the drawings, and are merely for conveniently describing the present application and simplifying the description, rather than indicating or implying that the device or element must have the specific orientation and be constructed and operated according to the specific orientation. Therefore, they should not be construed as a limitation on the present application.

In the description of the present disclosure, the terms "one embodiment", "some embodiments", "exemplary embodiment", "example", "specific example" or "some examples" are intended to indicate that specific features, structures, materials or characteristics related to the embodiment or example are comprised in at least one embodiment or example of the present application. The illustrative indication of the above terms does not necessarily refer to the same embodiment or example. Moreover, the specific features, structures, materials or characteristics may be comprised in any one or more embodiments or examples in any suitable manner.

In the embodiments of the present application, the meaning of "plurality of" is "two or more", and the meaning of "at least one" is "one or more", unless explicitly and particularly defined otherwise.

All of the features used in the embodiments of the present application of "parallel", "perpendicular", "the same" and so on include the features of "parallel", "perpendicular", "the same" and so on in the strict sense, and include the cases in which there is a certain tolerance such as "substantially parallel", "substantially perpendicular" and "substantially the same", taking into consideration the measurement and the tolerances relevant to the measurement on particular quantities (for example, restricted by the measuring system), and represent that they are in the acceptable deviation ranges of the particular values determined by a person skilled in the art. For example, the "substantially" can represent that they are within one or more standard deviations, or within 10% or 5% of the values.

Unless stated otherwise in the context, throughout the description and the claims, the term "comprise" is interpreted as the meaning of opened comprising, i.e., "including but not limited to".

The "same layer" according to the embodiments of the present application refers to the relation between multiple film layers that are formed by using the same material after the same step (for example, a one-step patterning step). The "same layer" used herein does not always refer to that the thickness of a plurality of film layers are equal or that the heights in a cross-sectional view of a plurality of film layers are equal. The polygons in the description are not the strictly defined polygons, may be an approximate triangle, parallelogram, trapezoid, pentagon, hexagon and so on, and may have some small deformations caused by tolerance.

It should be noted that all of the organism-relevant to-be-detected samples, detection processes, and so on, that are involved in the present application are acquired and performed with the consent of the subject himself/herself or the guardian thereof and in compliance with laws and regulations.

Unless particularly stated otherwise, as used herein, "nM" refers to "n mol/L", "μM" refers to "μmol/L", and "mM" refers to "m mol/L".

Acute myelogenous leukemia (AML) is a commonly seen acute leukemia, and its morbidity increases year by year (1.62/10 ten thousands). Acute myelocytic leukemia is a medullary-system hematopoietic stem cell/progenitor cell malignant disease, with paraplasm of the myeloid archaeocytes and juvenile cells in bone marrow and peripheral blood as the major characteristics. The clinical manifestation includes anemia, hemorrhage, infection and fever, visceral infiltration, metabolic disorder and so on. Most of the clinical cases have acute and severe states of illness and dangerous prognosis, and, if they are not treated in time, the disease can often be life-threatening. This disease accounts for 30% of leukaemia of childhood. In terms of the molecular biological changing and response to chemotherapy, the pediatric AML is similar to that of adult (<50 years old). Infant AML causes extramedullary leukemia more easily than that of adult.

AML has a high heterogeneity, and currently there has not been an effective method of early detection. Complete blood cell count and peripheral blood smear are the most commonly seen AML lookup methods. In the blood of most of the AML patients there are many immature leukocytes, while the erythrocytes or the thrombocytes are insufficient. However, those discoveries merely might serve as prompting, and cannot be used as the basis for definite diagnosis, and the definite diagnosis requires the combination with bone marrow biopsy, which causes pain of the patient. Therefore, a non-invasive, quick, high-sensitivity detecting method is currently a research hotspot in AML early diagnosis and prognosis.

The detection of protein-type tumor markers is of importance to the diagnosis, the efficacy observation, the recurrence determination, the metastasis and the prognosis determination of cancers. Most of solid tumors are derived from epithelial cells, and when the tumor cells are quickly differentiating and proliferating, some cell types or components that are not expressed in normal tissues emerge with a a large quantity, for example, keratin serving as the cytoskeleton, to become the tumor markers. The tumor markers whose chemical nature is the protein type include: enzymes; protein-type or peptide-type hormones; and other proteins which are not the above two types.

In view of that, the embodiments of the present application provide a detection base board and a detection chip, wherein the detection base board comprises a substrate; the substrate comprises a sample testing region; the sample testing region comprises a plurality of detecting units, each of the detecting units comprises a sensing unit and a signal generating unit, and the sensing unit and the signal generating unit are electrically connected; the sensing unit is configured to react with a sample to be detected and generate an electric signal, and the signal generating unit is configured to receive the electric signal and generate a detection current; the sensing unit comprises a pair of sensing electrodes, and the pair of sensing electrodes are electrically connected to the signal generating unit; and the contours of the sensing electrodes comprise an arc line.

In the detection base board according to the embodiments of the present application, by providing the plurality of detecting units, the different AML-relevant protein markers in the same sample to be detected can be identified simultaneously, to significantly increase the diagnosis accuracy, provide a high-efficiency clinical AML monitoring and detecting platform, and promote the development of individualized treatment. In addition, by configuring that both of the outer contours of the sensing electrodes comprise an arc line, the contact area between the active ingredients in the sample to be detected and the sensing unit can be increased, thereby increasing the detection sensitivity of the detecting units.

The detection base board and the detection chip according to the embodiments of the present application will be described particularly below with reference to the drawings.

As shown in FIG. 1, an embodiment of the present application provides a detection base board, wherein the detection base board comprises a substrate 100. The substrate 100 comprises a sample testing region A.

The sample testing region A comprises a plurality of detecting units 11, each of the detecting units 11 comprises a sensing unit 11B and a signal generating unit 11A, and the sensing unit 11B and the signal generating unit 11A are electrically connected. The sensing unit 11B is configured to react with a sample to be detected and generate an electric signal, and the signal generating unit 11A is configured to receive the electric signal and generate a detection current.

Figure 3:
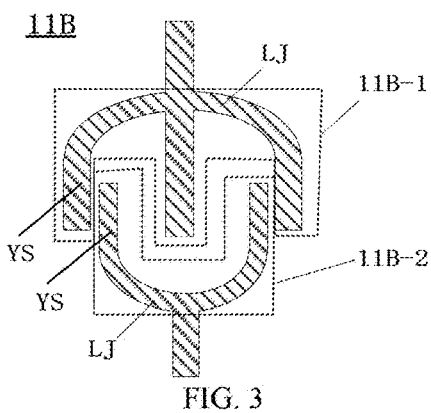
FIGS. 3 and 4 are schematic planar structural diagrams of two types of sensing units according to embodiments of the present application.
Figure 4:
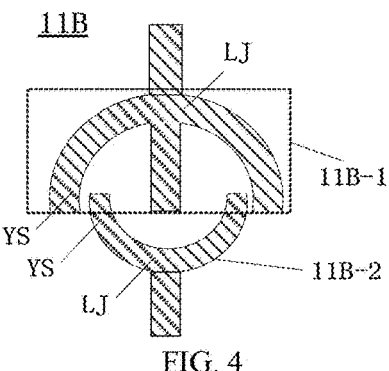

As shown in FIG. 3 or FIG. 4, the sensing unit 11B comprises a pair of sensing electrodes (for example, a sensing electrode 11B-1 and a sensing electrode 11B-2), and the pair of sensing electrodes (for example, the sensing electrode 11B-1 and the sensing electrode 11B-2) are electrically connected to the signal generating unit 11A. Both of the outer contours of the sensing electrodes (for example, the sensing electrode 11B-1 and the sensing electrode 11B-2) comprise an arc line.

In an exemplary embodiment, the substrate 100 of the detection base board may be a flexible substrate, and may also be a rigid substrate.

In some examples, the substrate 100 may be fabricated by using one or more of glass, polyimide, polycarbonate, polyacrylate, polyetherimide and polyether sulfone, and the present embodiment includes but is not limited thereto.

If the substrate 100 is a flexible substrate, the substrate 100 may comprise a single flexible-material layer, or the substrate 100 may comprise a first flexible-material layer, a first inorganic-non-metallic-material layer, a second flexible-material layer and a second inorganic-non-metallic-material layer that are arranged sequentially in stack.

If the substrate 100 is a rigid substrate, the substrate 100 may comprise a glass or a silicon material.

The shape of the planar pattern of the detection base board is not limited herein, and the shape of the planar pattern of the detection base board is the same as the shape of the planar pattern of the substrate 100. As an example, the shape of the planar pattern of the detection base board may be a circle, a square, a rectangle, a parallelogram, a pentagon, a hexagon and so on.

In the embodiments of the present application, the case is taken as an example for the description in which both of the shape of the planar pattern of the detection base board and the shape of the planar pattern of the substrate 100 are a rectangle.

As an example, the plurality of detecting units 11 are located inside the same cavity (for example, inside a cavity formed by the detection base board and the cover plate, which is not shown in FIG. 1).

Whether the types of the protein markers that the plurality of detecting units 11 identify are the same is not limited herein.

As an example, the plurality of detecting units 11 may be configured to identify the same AML-relevant protein marker. Alternatively, the plurality of detecting units 11 may be configured to identify different types of AML-relevant protein markers in the same sample to be detected.

The quantity of the detecting units 11 in one detection base board is not limited herein. If the plurality of detecting units 11 can be configured to identify different types of AML-relevant protein markers in the same sample to be detected, the quantity of the detecting units 11 is greater than or equal to the quantity of the protein markers that can be detected in the same sample to be detected.

As an example, taking an AML protein marker as an example, if the sample to be detected has 14 protein markers relevant to acute myelogenous leukemia, then the quantity of the detecting units 11 is greater than or equal to 14, and each of the detecting units 11 is configured to detect an individual protein marker.

In an exemplary embodiment, the sensing unit 11B is configured to sense the sample to be detected and generate a corresponding electric signal, and the signal generating unit 11A is configured to generate a detection current according to the electric signal generated by the sensing unit. The user of the detection base board may, according to the variation value of the detection current before the addition of the sample to be detected and after the addition of the sample to be detected, calculate the concentration of the corresponding protein marker.

The types of the protein markers in the sample to be detected that each of the detecting units 11 can detect are different, whereby the concentrations of different protein markers can be detected by using the same sample to be detected in the same detection base board, thereby increasing the detection efficiency and the detection accuracy.

It should be noted that, in order to enable each of the detecting units 11 to detect the protein markers of different types in the sample to be detected, the detecting units 11 embed antibody molecules that match with the protein markers of different types. Accordingly, each of the detecting units 11 embeds one type of the antibody molecules, and each type of the antibody molecules matches with one type of the protein markers, which can realize detecting the concentrations of the protein markers of different types by using the same sample to be detected.

In an exemplary embodiment, at least one side of the sample-detection region A is provided with a signal-detection region B, the signal-detection region B is provided with a plurality of first signal acquiring terminals 12 for the user to obtain the detection currents, and the first signal acquiring terminals 12 correspond to the signal generating units 11A one to one.

Particularly, each of the first signal acquiring terminals 12 is electrically connected to one of the signal generating units 11A, to transmit the detection current generated by the one signal generating unit 11A, so that the user obtains the detection currents of the different detecting units 11, thereby calculating the concentrations of the corresponding protein markers.

As an example, as shown in FIG. 3 or FIG. 4, the sensing electrode 11B-1 and the sensing electrode 11B-2 of the sensing unit 11B are not connected to each other (which means mechanical connection, and does not means electric connection).

As an example, as shown in FIG. 3 or FIG. 4, the structures of the sensing electrode 11B-1 and the sensing electrode 11B-2 of the sensing unit 11B are not completely the same, but both of the outer contours of the two sensing electrodes comprise an arc line. It should be noted that FIGS. 3 and 4 do not only illustrate the two sensing electrodes of the same sensing unit 11B, but also illustrate the lead wires connected to the two sensing electrodes, which should be explained particularly here.

The particular materials of the sensing electrode 11B-1 and the sensing electrode 11B-2 of the sensing unit 11B are not limited herein.

As an example, the materials of the sensing electrode 11B-1 and the sensing electrode 11B-2 of the sensing unit 11B may be a metal, for example, gold (Au) in a single layer, or chromium (Cr)/gold (Au) arranged in stack. In the detection base board according to the embodiments of the present application, as shown in FIG. 1, by providing the plurality of detecting units 11, the different AML-relevant protein markers in the same sample to be detected can be identified simultaneously, or the same AML-relevant protein marker can be identified multiple times, to significantly increase the diagnosis accuracy, provide a high-efficiency clinical AML monitoring and detecting platform, and promote the development of individualized treatment.

In practical applications, by using the surface-treatment layer provided on the sensing electrodes (the details of the surface-treatment layer will be described below), the sensing electrodes and the antibodies are connected together, and subsequently the corresponding protein markers are identified by using the antibodies. During the formation of the surface-treatment layer, the material of the surface-treatment layer easily has the coffee-ring effect, so that the active ingredients of the material of the surface-treatment layer are distributed mainly at the edge positions of the sensing electrodes in an arc shape, whereby the antibodies are also distributed mainly at the edge positions of the sensing electrodes. By configuring that both of the outer contours of the sensing electrodes (for example, the sensing electrode 11B-1 and the sensing electrode 11B-2 in FIG. 3 or FIG. 4) comprise an arc line, the contact area between the active ingredients in the sample to be detected and the sensing unit 11B can be increased, thereby increasing the detection sensitivity of the detecting units 11.

Figure 2:
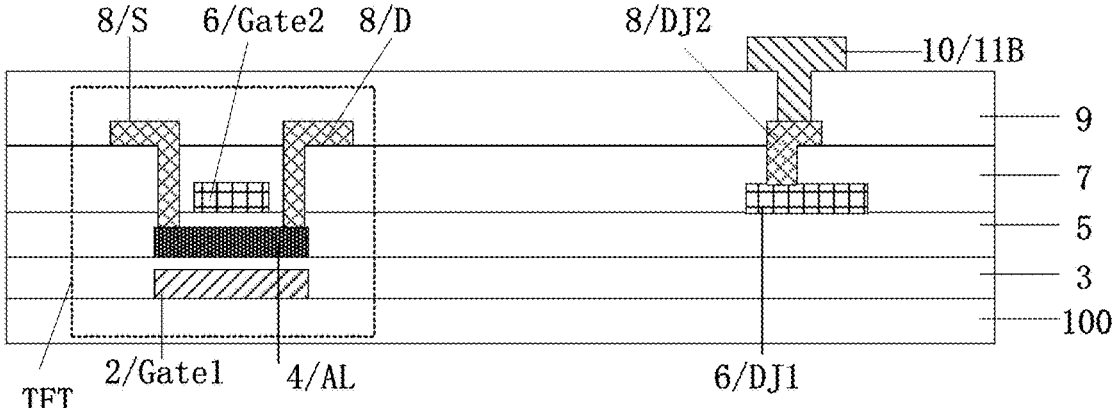
FIG. 2 is a schematic cross-sectional structural diagram along M1M2 direction in FIG. 1.

In at least one embodiment of the present application, referring to FIGS. 1 and 2, the signal generating unit 11A comprises a bigrid transistor (for example, TFT or MOS), and a first grid Gate1 and a second grid Gate2 of the bigrid transistor are configured to be connected to different electrically conducting components. FIG. 2 is a schematic cross-sectional structural diagram along M1M2 in FIG. 1.

In an exemplary embodiment, because a first grid Gate1 and a second grid Gate2 of the bigrid transistor are configured to be connected to different electrically conducting components, at least within the detection time period, the electric potentials on the first grid Gate1 and the second grid Gate2 of the bigrid transistor are unequal.

As an example, the bigrid transistor may be a Thin-Film Transistor (referred to for short as TFT). Alternatively, the bigrid transistor may be a Metal Oxide Semiconductor Field Effect Transistor (MOSFET), which is referred to for short as a MOS transistor.

As an example, as shown in FIG. 2, the bigrid transistor comprises the first grid Gate1, the second grid Gate2, an active part AL, a source S and a drain D.

In the embodiments and the drawings of the present application, the case is taken as an example for the illustration and the description in which the bigrid transistor is a TFT transistor.

It should be noted that the usage method is different from that of a conventional bigrid transistor. Conventionally, both of the two grids of a bigrid transistor are connected to the same electrically conducting component; in other words, the two grids of the bigrid transistor are electrically connected together, and always have equal electric potentials. In the embodiments of the present application, the two grids of the bigrid transistor are connected to different electrically conducting components, so that, at least within the detection time period, the electric potentials on the first grid Gate1 and the second grid Gate2 of the bigrid transistor are unequal, whereby the electric currents passing through the bigrid transistor within the detection time period and the non-detection time period are unequal, thereby calculating the concentrations of the corresponding protein markers detected by the detecting units 11 according to the variation of the detection currents.

Figure 7:
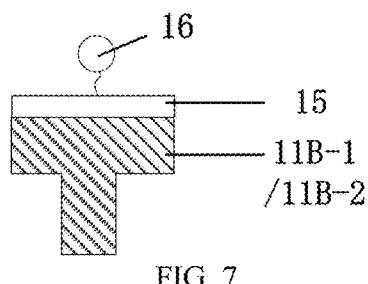
FIG. 7 is a schematic cross-sectional structural diagram of a sensing unit according to an embodiment of the present application.

In at least one embodiment of the present application, as shown in FIG. 7, the sensing unit 11B further comprises an antibody 16 located on the pair of sensing electrodes 11B-1, 11B-2, and the antibody 16 and the sensing electrodes 11B-1, 11B-2 are configured to be connected by covalent bonds. The types of the antibodies on the pairs of sensing electrodes 11B-1, 11B-2 are different.

Antibodies refer to proteins that are generated by the body due to the stimulation by antigens and have the effect of protection. They (immune globulin is not merely an antibody) are large-sized Y-shaped proteins that are secreted by plasmacytes (effector B cells) and used by the immune system to identify and neutralize foreign matters such as bacteria and viruses. An antibody can identify a unique characteristic of a particular foreign matter, wherein the foreign matter is referred to as an antigen.

In the embodiments of the present application, the antibodies are connected to the sensing electrodes by covalent bonds (the antibodies 16 corresponding to each of the detecting units 11 are of different types). In the disease detection using the detection base board, the antibody can have a biochemical reaction with the protein marker, to generate an electric signal (electric current), and the electric current is transmitted via the sensing electrode to the second grid Gate2 of the bigrid transistor (the sensing electrode is electrically connected to the second grid Gate2 of the bigrid transistor). At this point, the electric current passing through the bigrid transistor changes. According to the variation value of the electric current passing through the bigrid transistor, the concentration of the corresponding protein marker can be calculated, and, subsequently, according to the concentration, it is determined whether the detection result is "negative" or "positive".

In the embodiments of the present application, the protein markers may include protein markers relevant to acute myelogenous leukemia, for example, milk-fat-globule surface growth factor (MFC-E8), interleukin 20 (IL-20), IL-3, IL-2 R alpha, IL-2 R beta/CD122, IL-1 R6/IL-1 Rrp2, tumor necrosis factor α (TNF-alpha), ostein (Osteoactivin), glucocorticoid-induced tumor-necrosis-factor receptor (GITR/TNFRF18), insulin receptor (Insulin R), macrophage colony stimulating factor (M-CSF), macrophage colony stimulating factor receptor (M-CSF R), specific hepatocyte proliferative factor (Hepassocin), and secondary lymphoid tissue chemokine (6Ckine).

The "covalent bond" is a type of chemical bonds. Two or more atoms share their outer-shell electrons, and, in an ideal state, reach the state of electron saturation, thereby forming a stable chemical structure. Such a strong effect between several adjacent atoms and the shared electrons is referred to as a covalent bond.

In practical applications, because the material of the sensing electrodes is an electrically conductive material, for example, a metal or a metal oxide, which has difficulty in forming covalent bonds directly with the antibody 16, as shown in FIG. 7, in at least one embodiment of the present application, the sensing unit 11B further comprises a surface-treatment layer 15, the surface-treatment layer 15 covers the pair of sensing electrodes 11B-1, 11B-2, and the surface-treatment layer 15 is configured to form the covalent bonds with the antibodies 16.

In practical applications, by providing the surface-treatment layer on the sensing electrodes, the sensing electrodes and the antibodies are connected together, and subsequently the corresponding protein markers are identified by using the antibodies. During the formation of the surface-treatment layer, the material of the surface-treatment layer easily has the coffee-ring effect, so that the active ingredients of the material of the surface-treatment layer are distributed mainly at the edge positions of the sensing electrodes, whereby the antibodies are also distributed mainly at the edge positions of the sensing electrodes.

It should be noted that the coffee-ring effect refers to the phenomenon that, when a drop of coffee or tea is dripped onto a table top, its particulate matter leaves a stained blot on the table top, and the color of the blob is not even, wherein the color of the edge part is darker than that of the center part, to form an annular spot. In a solution, in order to maintain the area of a liquid drop constant, a flow from the center to the outer side is generated, and that flow brings the solute of the solution to the contact line to deposit, thereby finally forming an annular deposit. The material solution of the surface-treatment layer, when dripped onto the sensing electrodes. also has such a "coffee-ring effect".

In at least one embodiment of the present application, the material of the surface-treatment layer 15 comprises mercaptopropylamine or ethylamine.

Antibodies refer to proteins that are generated by the body due to the stimulation by antigens and have the effect of protection. Moreover, the proteins in organisms are obtained by forming one or more peptide chains from multiple α-amino acids (for example, 20) by dehydrated condensation and subsequently forming complicated space structures by coiling and folding of the peptide chains. The proteins have no constant chemical formulas, and they are a type of nitrogen-containing biomacromolecules, have high molecular weights and complicated structures, and are usually formed by the elements of C, H, O, N and S.

By configuring that the material of the surface-treatment layer 15 comprises mercaptopropylamine or ethylamine, the amido groups in the mercaptopropylamine or ethylamine can form covalent bonds with the antibody, thereby tightly connecting the antibody 16 to the surface of the sensing electrodes 11B-1, 11B-2 by using the surface-treatment layer 15.

As an example, in practical applications, the process may comprise spread-coating a solution of mercaptopropylamine or ethylamine to the surfaces of the sensing electrodes 11B-1, 11B-2, and standing at approximately 4° C. (±2° C.) for 20 h-28 h (for example, 24 h); subsequently washing by using PBS buffer solutions of different concentrations (for example, washing by using PBS buffer solutions of the two concentrations of 10× and 1×); subsequently washing by using clear water (for example, distilled water or deionized water); mixing the 14 antibodies corresponding to the above-described 14 protein markers individually with a 1:1 solution of EDC and NHS, dropping the miscible liquids onto 14 different sensing units 11B, and standing at approximately 15° C. (±2° C.) for 30 min±10 min; finally washing by using PBS buffer solutions of the two concentrations of 10× and 1×; and subsequently washing by using clear water (for example, distilled water or deionized water), so as to successfully connect the different types of antibodies onto the sensing units 11B.

The PBS buffer solution is the most extensively used buffer solution in biochemistry, with $Na_2HPO_4$, $KH_2PO_4$, NaCl and KCl as the essential components, and is generally used as a solvent, to dissolve and protect the reagents. EDC refers to 1-(3-dimethylaminopropyl)-3-ethylcarbodiimide hydrochloride, and is referred to for short as EDC hydrochloride. NHS refers to N-hydroxysuccinimide. In at least one embodiment of the present application, as shown in FIG. 3 or FIG. 4, each of the sensing electrodes 11B-1, 11B-2 comprises a plurality of extending parts YS and a connecting part LJ connecting the extending parts YS. In the same sensing electrode 11B-1 or 11B-2, the connecting part LJ is located on the same side of the extending parts YS.

In FIG. 3 or FIG. 4, in the same sensing electrode, the extending parts YS refer to the components of the sensing electrode that extend in the vertical direction, and the connecting part LJ refers to the component that has a direction of extension intersecting with the direction of extension of the extending parts YS and connects all of the extending parts YS together.

The sensing unit comprises a first sensing electrode 11B-2 and a second sensing electrode 11B-1, the pattern of the orthographic projection on the substrate 100 of the connecting part LJ of the first sensing electrode 11B-2 and two extending parts YS connected to the two ends of the connecting part LJ is a first arch, the pattern of the orthographic projection on the substrate 100 of the connecting part LJ of the second sensing electrode 11B-1 and two extending parts YS connected to the two ends of the connecting part LJ is a second arch, and the two ends of the first arch extend into the region enclosed by the second arch.

As an example, taking the structure of the sensing unit 11B shown in FIG. 3 as an example, the pattern of the orthographic projection on the substrate 100 of the combination between the two extending parts YS and the one connecting part LJ of the first sensing electrode 11B-2 is the first arch, and the pattern of the orthographic projection on the substrate 100 of the combination between the two extending parts YS on the two sides and the one connecting part LJ of the second sensing electrode 11B-1 is the second arch, wherein the dimension of the second arch perpendicular to the direction of extension of the extending parts YS of the second sensing electrode 11B-1 is greater than the dimension of the first arch perpendicular to the direction of extension of the extending parts YS of the first sensing electrode 11B-2, and the direction of extension of the extending parts YS of the first sensing electrode 11B-2 and the direction of extension of the extending parts YS of the second sensing electrode 11B-1 are the same.

In some embodiments, the first arch does not completely comprise an arc line, and the first arch may comprise an arc line, and may also comprise a straight line. The second arch does not completely comprise an arc line, and the second arch may comprise an arc line, and may also comprise a straight line.

That the two ends of the first arch extend into the region enclosed by the second arch, referring to FIGS. 3 and 4, may be understood as that at least part of the regions of the two extending parts YS of the first sensing electrode 11B-2 individually extend to the region enclosed by the second arch.

In at least one embodiment of the present application, the quantity of the extending parts YS of the first sensing electrode (for example, 11B-2) is at least two, the quantity of the extending parts YS of the second sensing electrode (for example, 11B-1) is at least three, and the extending parts YS of the first sensing electrode (for example, 11B-2) and the extending parts YS of the second sensing electrode (for example, 11B-1) are alternately arranged. The shape of the pattern of the orthographic projection of each of the connecting parts LJ on the substrate 100 comprises an arc shape.

As an example, as shown in FIGS. 3 and 4, the sensing electrode 11B-1 comprises 3 extending parts YS, and the sensing electrode 11B-2 comprises 2 extending parts YS.

Whether the shapes of the patterns of the orthographic projections of the extending parts YS on the substrate 100 comprise an arc shape is not limited herein.

As an example, as shown in FIG. 3, regarding the sensing electrodes 11B-1, 11B-2, the shape of the pattern of the orthographic projection on the substrate 100 of the connecting part LJ is an arc shape, and the shapes of the patterns of the orthographic projections on the substrate 100 of the extending parts YS are rectangles.

As an example, as shown in FIG. 4, the shape of the pattern of the orthographic projection on the substrate 100 of the connecting part LJ is an arc shape, and the shapes of the patterns of the orthographic projections on the substrate 100 of the extending parts YS are also arc shapes.

Particularly, regarding the sensing electrode 11B-1, the pattern of the orthographic projection on the substrate 100 of the combination between its connecting part LJ and the two extending parts YS on the outer side is a semi-round-ring shape (or semi-elliptical-ring shape). Regarding the sensing electrode 11B-2, the pattern of the orthographic projection on the substrate 100 of the combination between its connecting part LJ and the two extending parts YS is a semi-round-ring shape (or semi-elliptical-ring shape).

In at least one embodiment of the present application, as shown in FIG. 3 or FIG. 4, the shape of the pattern of the orthographic projection of the first sensing electrode 11B-2 on the substrate 100 is a U shape, the shape of the pattern of the orthographic projection on the substrate 100 of the connecting part LJ of the second sensing electrode 11B-1 is an arc shape, and the shape of the pattern of the orthographic projection on the substrate 100 of each of the extending parts YS of the second sensing electrode 11B-1 is a rectangle.

It should be noted that the above-described "U shape" is a U shape in the board sense, and is not the U shape in the strict sense, and U-like shapes that are obtained by transformation on the basis of a U shape also fall within protection scope of the present application.

It should also be noted that the shape of the pattern of the orthographic projection on the substrate 100 of the second sensing electrode 11B-1 is an "E shape". The above-described "E shape" is an E shape in the board sense, and is not the E shape in the strict sense, and E-like shapes that are obtained by transformation on the basis of an E shape also fall within the protection scope of the present application.

In the embodiments of the present application, according to the above-described coffee-ring effect of the solution of the material of the surface-treatment layer 15, by configuring that, in the same sensing unit 11B, the shape of the pattern of the orthographic projection of the first sensing electrode 11B-2 on the substrate 100 is a U shape, and the shape of the pattern of the orthographic projection on the substrate 100 of the connecting part LJ of the second sensing electrode 11B-1 is an arc shape, the contact area between the active ingredients in the sample to be detected and the sensing unit 11B can be increased, thereby increasing the detection sensitivity of the detecting units 11. In addition, the second sensing electrode 11B-1 and the first sensing electrode 11B-2 according to the embodiments of the present application have simple structures, a low design cost, and a low difficulty in the fabrication.

When used for the detection and diagnosis of acute myelogenous leukemia, the sample to be detected may be "blood", including but not limited to whole blood or an isolate obtained from blood.

In at least one embodiment of the present application, referring to FIGS. 1 and 2, the first grid Gate1 of the bigrid transistor is electrically connected to a constant-voltage-signal inputting terminal (not shown in the figures), and the first grid Gate1 is configured to control the turning-on and turning-off of the bigrid transistor. The second grid Gate2 of the bigrid transistor is electrically connected to the pair of sensing electrodes 11B-1, 11B-2, and the second grid Gate2 is configured to, according to the electric signals generated in the sensing electrodes 11B-1, 11B-2, control the variation of the electric current in the bigrid transistor and simultaneously generate the detection current.

It should be noted that, in the practical detection, the first grid Gate1 controls the bigrid transistor to be conducted, and the channel region of the bigrid transistor generates the initial current $I_0$. When the protein marker and the antibody react and generates the electric current, the electric current is transmitted via the sensing electrode to the second grid Gate2, and the electric potential on the second grid Gate2 changes, whereby the electric-current value of the electric current flowing through the channel region of the bigrid transistor changes (the detection current I-the initial current $I_0$), and the concentration of the corresponding protein marker is calculated according to the variation value of the electric current.

In an exemplary embodiment, the area of the planar pattern of the second grid Gate2 of the bigrid transistor is greater than the area of the planar pattern of the pair of sensing electrodes. If the areas of them have a large difference, in the transmission of the electric signal, the second grid Gate2 can amplify the electric signals transmitted by the pair of sensing electrodes, thereby improving the accuracy of the detection.

In at least one embodiment of the present application, as shown in FIG. 1, the signal-detection region B further comprises at least one negative electrode terminal 13. The negative electrode terminal 13 is electrically connected to the second grid Gate2 by the sensing electrodes 11B-1, 11B-2.

The particular mode of the electric connection between the negative electrode terminal 13 and the second grid Gate2 by the sensing electrodes 11B-1, 11B-2 is not limited herein.

As an example, the negative electrode terminal 13 may be electrically connected to the sensing electrodes by leads provided in the same layer as the sensing electrodes, the sensing electrodes and the second grid Gate2 are located at different electrically conducting film layers, and the sensing electrodes and the second grid Gate2 may be electrically connected together by via holes (also referred to as the through holes, Via).

It should be noted that, in some examples, the negative electrode terminal 13 may be electrically connected to one of the sensing electrodes of one sensing unit 11B.

In practical applications, when the first grid Gate1 and the second grid Gate2 of the bigrid transistor are being applied with a voltage simultaneously, referring to FIG. 2, a built-in capacitor is formed between the first grid Gate1 and the second grid Gate2. With the increasing of the duration of the voltage application on the second grid Gate2, a large quantity of electric charges are accumulated inside the bigrid transistor, which interferes the electric current of the bigrid transistor. Accordingly, in at least one embodiment of the present application, the negative electrode terminal 13 is electrically connected to a correcting line, and the negative electrode terminal 13 is configured to release the electric charges inside the bigrid transistor to correct the bigrid transistor.

In an exemplary embodiment, if positive charges of a large quantity are accumulated inside the bigrid transistor, the correcting line may comprise an earthing line. If negative charges of a large quantity are accumulated inside the bigrid transistor, the correcting line may comprise an anode signal line. It should be noted that, throughout the subsequent relevant description of the embodiments of the present application, the case is taken as an example for the description in which a large quantity of positive charges are accumulated inside the bigrid transistor.

In the embodiments of the present application, the second grid Gate2 is earthed via sequentially one of the sensing electrodes of the sensing unit 11B and the negative electrode terminal 13, whereby all of the electric charges inside the bigrid transistor can be discharged, thereby simply and quickly correcting the bigrid transistor, preventing interference by the electric charges inside the bigrid transistor on the electric current flowing through the bigrid transistor, and thus preventing interference with the variation value of the detection current, which increases the detection accuracy of the detecting unit 11, and increases the detection efficiency.

Figure 5:
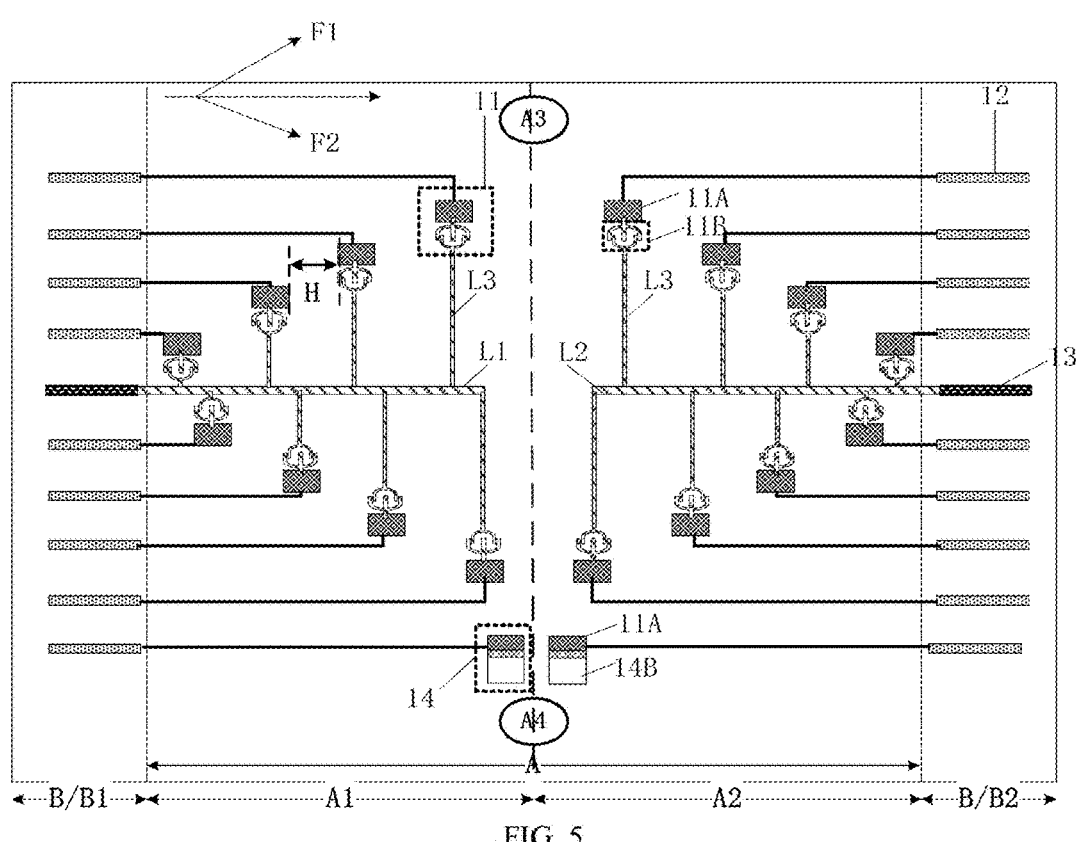
FIGS. 5 and 6 are schematic planar structural diagrams of another two types of detection base boards according to embodiments of the present application.

In at least one embodiment of the present application, as shown in FIG. 5, the substrate 100 further comprises a signal-detection region B located on at least one side of the sample-detection region A, the signal-detection region B comprises a plurality of first signal acquiring terminals 12, the first signal acquiring terminals 12 are electrically connected to the signal generating units 11A, and the quantity of the first signal acquiring terminals 12 is equal to the quantity of the signal generating units 11A.

Figure 8:
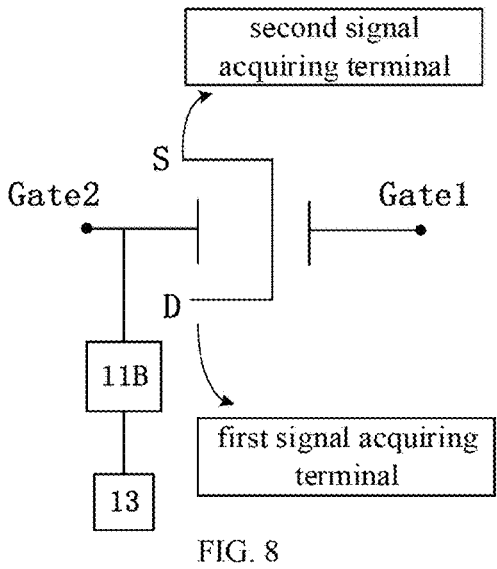
FIG. 8 is a diagram illustrating the principle of the checking of a detection base board according to an embodiment of the present application.

The signal-detection region B further comprises a plurality of second signal acquiring terminals. As shown in FIG. 8, in each of the detecting units 11, a drain D of the bigrid transistor is electrically connected to the first signal acquiring terminal 12, a source S of the bigrid transistor is electrically connected to the second signal acquiring terminal (not labeled), the first signal acquiring terminal 12, the drain D of the bigrid transistor, the source S of the bigrid transistor and the second signal acquiring terminal are configured to form an electrically conducting loop, and the detection current refers to the electric current in the loop within a detection time period.

It should be noted that, as shown in FIG. 5, FIG. 5 merely illustrates a schematic diagram of the leads electrically connecting the bigrid transistors and the first signal acquiring terminals 12, and does not illustrate a schematic diagram of the leads electrically connecting the bigrid transistor and the second signal acquiring terminals. The positions and the arrangement of the plurality of second signal acquiring terminals of the detection base board are not limited herein, and may be configured particularly according to practical rooms. The positions and the arrangement of the plurality of first signal acquiring terminals 12 of the detection base board are not limited herein, and may be configured particularly according to practical rooms.

Figure 6:
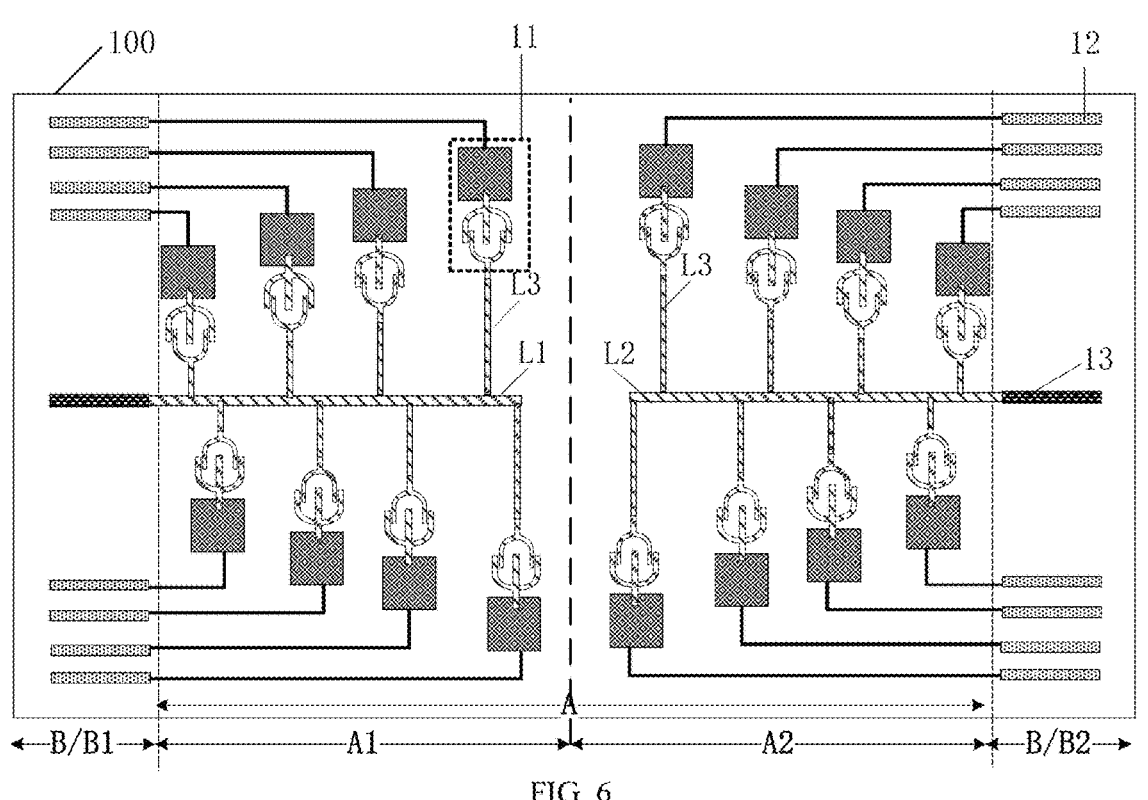

As an example, as shown in FIGS. 5 and 6, the plurality of first signal acquiring terminals 12 may be evenly distributed.

In FIG. 5, the plurality of first signal acquiring terminals 12 and the negative electrode terminal 13 may be distributed equidistantly. Alternatively, as shown in FIG. 6, the plurality of first signal acquiring terminals 12 may be distributed equidistantly, and the minimum distance from the negative electrode terminal 13 to the first signal acquiring terminals 12 is greater than the minimum distance between two neighboring first signal acquiring terminals 12.

In addition, the positions of the film layers where the leads between the source S of the bigrid transistor and the second signal acquiring terminals are located are not limited herein, and the positions of the film layers where the leads between the drain D of the bigrid transistor and the first signal acquiring terminal 12 are located are not limited herein. They may be located in any one of the electrically conducting layers of the detection base board. Referring to FIG. 2, the leads may be located in at least one of a first electrically conducting layer 2, a second electrically conducting layer 6, a source-drain electrically conducting layer 8 and a third electrically conducting layer 10, which may be decided particularly according to the design room and the fabricating process.

In at least one embodiment of the present application, as shown in FIG. 5, the sample testing region B comprises at least one reference unit 14, and the reference unit 14 comprises a reference electrode 14B and the bigrid transistor 11A.

In the reference unit 14, the first grid Gate1 of the bigrid transistor is electrically connected to the constant-voltage-signal inputting terminal, the first grid Gate1 is configured to control the turning-on and turning-off of the bigrid transistor, and the second grid Gate2 of the bigrid transistor is electrically connected to the reference electrode 14B. In addition, as similar to the bigrid transistor in the detecting units 11 described above, a drain D of the bigrid transistor in the reference unit 14 is electrically connected to the first signal acquiring terminal, and a source S of the bigrid transistor is electrically connected to the second signal acquiring terminal.

In an exemplary embodiment, the reference unit 14 serves as the blank control group in the detection, to detect a background signal, to increase the detection accuracy, and eliminate interference by external factors.

In some embodiments, the reference electrode 14B may be configured to have totally the same structure, size and material as those of the sensing unit 11B. For example, the structure of the reference electrode 14B may be similar to the pair of sensing electrodes in FIG. 3 or FIG. 4, and the material may be the same as the material of the sensing electrodes, which is gold (Au).

In some other embodiments, in order to simplify the design, it may be configured that the planar pattern of the reference electrode 14B is a polygon, for example, a quadrangle. It may be configured that the material of the reference electrode 14B is silver (Ag)/silver chloride (AgCl) arranged in stack. Because silver chloride (AgCl) is unstable, a protecting layer may cover the silver chloride (AgCl), wherein the material of the protecting layer may be a resin, for example, polyvinyl butyral.

In practical applications, the second grid Gate2 of the bigrid transistor may directly contact the reference electrode 14B. Particularly, the fabricating process may comprise directly dip-coating a silver colloid onto the second grid Gate2, heating at 75° C. for approximately 15 min to evaporate the solvent, dropping a 0.1 m $FeCl_3$ solution onto the silver colloid to react for approximately 4 min to form an AgCl layer, and, subsequently, at room temperature, treating the surface of the AgCl electrode by using a PVB methanol solution for 3 hours to form the protecting layer.

In the embodiments of the present application, the main function of the reference electrode 14B is to provide a stable electrode potential, and whether the material and the structure are the same as those of the sensing electrodes is not limited. In order to simplify the design and improve the stability of the electric potential of the reference electrode 14B, it is preferably configured that the material of the reference electrode 14B is silver (Ag)/silver chloride (AgCl) arranged in stack, and a protecting layer covers the reference electrode 14B, which should be explained particularly here.

In at least one embodiment of the present application, as shown in FIGS. 5 and 6, the sample testing region A comprises a first sub-region A1 and a second sub-region A2. The substrate 100 comprises a first signal-detection sub-region B1 and a second signal-detection sub-region B2 that are located on the two sides of the sample testing region A. Each of the first sub-region A1 and the second sub-region A2 comprises eight detecting units 11.

Within the first sub-region A1, four detecting units 11 are arranged in a first direction F1, and the other four detecting units 11 are arranged in a second direction F2, wherein the first direction F1 and the second direction F2 intersect. The first direction F1 and the direction from the first sub-region A1 pointing to the second sub-region A2 (the direction pointed by the dotted-line arrow in FIG. 5) form an acute angle therebetween, and the second direction F2 and the direction from the first sub-region A1 pointing to the second sub-region A2 (the direction pointed by the dotted-line arrow in FIG. 5) form an acute angle therebetween. The included angle between the first direction F1 and the second direction F2 is also an acute angle.

The arrangement of the detecting units 11 within the second sub-region A2 and the arrangement of the detecting units 11 within the first sub-region A1 are symmetrical.

In at least one embodiment of the present application, as shown in FIGS. 5 and 6, the first sub-region A1 comprises one first trace L1, the second sub-region A2 comprises one second trace L2, and the first trace L1 and the second trace L2 have equal lengths and are arranged symmetrically. Both of the first trace L1 and the second trace L2 extend in the direction from the first sub-region A1 pointing to the second sub-region A2 (the direction pointed by the dotted-line arrow in FIG. 5).

The first trace L1 is configured to connect the eight detecting units 11 within the first sub-region A1 together in series, and the second trace L2 is configured to connect the eight detecting units 11 within the second sub-region A2 together in series.

In at least one embodiment of the present application, as shown in FIGS. 5 and 6, the first signal-detection sub-region B1 is located on the side of the first sub-region A1 away from the second sub-region A2, and the second signal-detection sub-region B2 is located on the side of the second sub-region A2 away from the first sub-region A1.

The first signal-detection sub-region B1 comprises a first negative electrode terminal (the negative electrode terminal 13 located within the first signal-detection sub-region B1 is referred to as the first negative electrode terminal), the second signal-detection sub-region B2 comprises a second negative electrode terminal (the negative electrode terminal 13 located within the second signal-detection sub-region B2 is referred to as the second negative electrode terminal), all of the second grids Gate2 of all of the bigrid transistors within the first sub-region A1 are electrically connected to the first negative electrode terminal by sequentially the sensing electrodes and the first trace L1, and all of the second grids Gate2 of all of the bigrid transistors within the second sub-region A2 are electrically connected to the second negative electrode terminal by sequentially the sensing electrodes and the second trace L2.

In an exemplary embodiment, as shown in FIG. 5 or 6, both of the first trace L1 and the second trace L2 are traces that extend in the horizontal direction. Besides them, the detection base board is further provided with a plurality of third traces L3 extending in the vertical direction, to connect the first trace L1 (or the second trace L2) and the sensing electrodes.

As an example, the first trace L1 and the second trace L2 may be arranged in the same layer.

As an example, the first trace L1 and the second trace L2 may be provided in the same layer as the sensing electrodes 11B-1, 11B-2.

In the embodiments of the present application, by connecting the eight detecting units 11 within the first sub-region A1 together in series by using the first trace L1, subsequently electrically connecting all of the second grids Gate2 of all of the bigrid transistors of the eight detecting units 11 to the first negative electrode terminal by sequentially the sensing electrodes and the first trace L1, and subsequently connecting the first negative electrode terminal to the ground terminal, the quantity of the traces in the detection base board can be reduced, and the electric charges accumulated in all of the bigrid transistors are discharged altogether, to eliminate static electricity, which, while ensuring the stable characteristics of all of the bigrid transistors, reduces the quantity of the traces, and saves the design room of the detection base board.

In at least one embodiment of the present application, as shown in FIG. 5, within the first sub-region A1 or the second sub-region A2, in the direction parallel to the plane where the substrate 100 is located, the minimum distance H between any two neighboring sensing units 11 is greater than or equal to 1.2 cm.

In an exemplary embodiment, within the first sub-region A1, the minimum distance between any two neighboring sensing units 11 is substantially equal.

In an exemplary embodiment, within the second sub-region A2, the minimum distance between any two neighboring sensing units 11 is substantially equal.

As an example, the minimum distance H between any two neighboring sensing units 11 may be 1.3 cm, 1.4 cm, 1.5 cm, 1.6 cm, 1.7 cm, 1.8 cm, 1.9 cm, and 2.0 cm.

TABLE 1

| situations of interference with different minimum distances H between two neighboring sensing units | | | | | | | | | |
|---|---|---|---|---|---|---|---|---|---|
| H/cm | 1.0 | 1.1 | 1.2 | 1.3 | 1.4 | 1.5 | 1.6 | 1.7 | 1.8 |
| Whether interference exists | yes | yes | no | no | no | no | no | no | no |

In at least one embodiment of the present application, as shown in FIG. 5, the detection base board further comprises a plurality of third traces L3, and the direction of extension of the third traces L3 intersects with the first trace L1. Some of the third traces L3 are configured to connect the first trace L1 and the detecting units 11 within the first sub-region A1, and the other of the third traces L3 are configured to connect the second trace L2 and the detecting units 11 within the second sub-region A2.

Both of the range of the lengths of the traces between the detecting units 11 and the first negative electrode terminal within the first sub-region A1 and the range of the lengths of the traces between the detecting units 11 and the second negative electrode terminal within the second sub-region A2 are 0.5 cm–5 cm.

In an exemplary embodiment, as shown in FIG. 5 or 6, both of the first trace L1 and the second trace L2 are traces that extend in the horizontal direction. Besides them, the detection base board is further provided with a plurality of third traces L3 extending in the vertical direction, to connect the first trace L1 (or the second trace L2) and the sensing electrodes.

As an example, the third traces L3 may be provided in the same layer as the first trace L1 and the second trace L2.

As an example, the first trace L1 and the second trace L2 have equal lengths.

As an example, the lengths of the traces connecting the detecting units 11 and the first negative electrode terminal within the first sub-region A1 and the lengths of the traces connecting the detecting units 11 and the second negative electrode terminal within the second sub-region A2 may be 0.6 cm, 1.0 cm, 1.3 cm, 1.5 cm, 1.8 cm, 2.0 cm, 2.5 cm, 2.8 cm, 3.0 cm, 3.5 cm, 3.8 cm, 4.0 cm, 4.3 cm, 4.5 cm or 4.8 cm.

Whether the lengths of the traces between the detecting units 11 and the first negative electrode terminal within the first sub-region A1 and the lengths of the traces between the detecting units 11 and the second negative electrode terminal within the second sub-region A2 are equal is not limited herein, and may be decided particularly according to practical situations.

As an example, the lengths of the two parts of the traces that are symmetrical with respect to each other may be substantially equal.

TABLE 2

| influence on the sensitivity by the lengths of the traces between the detecting units and the first negative electrode terminal within the first sub-region | | | | | | | | | |
|---|---|---|---|---|---|---|---|---|---|
| Length/cm | 0.4 | 0.5 | 1.0 | 1.5 | 2.0 | 2.5 | 3.0 | 4.5 | 5.0 | 5.3 |
| Sensitivity | high | high | high | high | high | high | high | high | high | low |

In the embodiments of the present application, it can be known according to the data in Table 1 that, by configuring that the minimum distance H between two neighboring sensing units 11 is greater than or equal to 1.2 cm, it is prevented that, in the fabrication of the detection base board, for example, when the antibodies 16 are being connected, the antibodies of different types interfere each other, thereby increasing the fabrication yield of the detection base board, and reducing the difficulty in the fabrication.

It can be known according to Table 2 that, if the lengths of the traces between the detecting units 11 and the first negative electrode terminal are lower, the calibration of the bigrid transistors has a better effect, and, in the practical detection, they have a higher detection sensitivity. It can be known according to the data in Table 2 that, if the lengths of the traces between the detecting units 11 and the first negative electrode terminal are greater than 5.0 cm, because of the influence by the resistances of the traces themselves on the effect of the discharging of the bigrid transistors, the detection sensitivity of the detecting units 11 decreases. Therefore, the upper limit value of the lengths of the traces between the detecting units 11 and the first negative electrode terminal is set to be 5 cm.

TABLE 3 influence on the detection sensitivities of different detecting units by the difference in the lengths of the traces between the detecting units and the first negative electrode terminal within the first sub-region

| Length difference/cm | 0.1 | 0.5 | 1.0 | 1.5 | 2.0 | 2.5 | 3.0 | 3.5 | 4.0 | 4.5 | 5.0 |
|---|---|---|---|---|---|---|---|---|---|---|---|
| Sensitivity difference | low | low | low | low | low | low | low | low | low | low | high |

In Table 3, the length difference refers to the difference between the length of the trace between one detecting unit and the first negative electrode terminal within the first sub-region and the length of the trace between another of detecting unit and the first negative electrode terminal. If the length difference is higher, the difference between the sensitivities of the two detecting units is higher, and it is difficult to balance the sensitivities of the detecting units of the detection base board. It can be known from the data of the length difference in Table 3 that, if the length difference is greater than 4.5 cm, the sensitivity difference of the detecting units is higher. By referring to, as described above, that the upper limit value of the lengths of the traces between the detecting units 11 and the first negative electrode terminal is set to be 5 cm, the lower limit value of the lengths of the traces between the detecting units 11 and the first negative electrode terminal is set to be 0.5 cm.

In addition, the configuration of the lengths of the traces between the detecting units 11 and the second negative electrode terminal within the second sub-region A2 is similar to that of the first sub-region A1, and is not discussed further.

In the embodiments of the present application, by configuring that both of the range of the lengths of the traces between the detecting units 11 and the first negative electrode terminal within the first sub-region A1 and the range of the lengths of the traces between the detecting units 11 and the second negative electrode terminal within the second sub-region A2 are 0.5 cm–5 cm, it is prevented that the wiring distances between different detecting units 11 and the negative electrode terminal 13 have an excessively high difference, thereby alleviating the adverse affection on the detection sensitivities of detecting units 11 by the difference in the trace length.

In at least one embodiment of the present application, as shown in FIG. 2, the detection base board comprises a first electrically conducting layer 2, a first insulating layer 3, a semiconductor layer 4, a second insulating layer 5, a second electrically conducting layer 6, a third insulating layer 7, a source-drain electrically conducting layer 8, a fourth insulating layer 9 and a third electrically conducting layer 10 that are located on the substrate 100 and are sequentially arranged. The first electrically conducting layer 2 comprises the first grids Gate1 of the bigrid transistors, the semiconductor layer 4 comprises active parts AL of the bigrid transistors, the second electrically conducting layer 6 comprises the second grids Gate2 of the bigrid transistors and a plurality of first connecting electrodes DJ1, and the source-drain electrically conducting layer 8 comprises the sources S and the drains D of the bigrid transistors and a plurality of second connecting electrodes DJ2.

The sensing electrodes 11B-1, 11B-2 are electrically connected to the second grids Gate of the bigrid transistors by sequentially the second connecting electrodes DJ2 and the first connecting electrodes DJ1.

As an example, the material of the first electrically conducting layer 2 may be a metal, for example, molybdenum (Mo).

As an example, the material of the first insulating layer 3 may be an inorganic material, for example, at least one of silicon nitride, silicon oxide and silicon oxynitride.

As an example, the material of the semiconductor layer 4 may be a metal oxide, for example, indium gallium zinc oxide (IGZO).

As an example, the material of the second insulating layer 5 may be an inorganic material, for example, at least one of silicon nitride, silicon oxide and silicon oxynitride.

As an example, the material of the second electrically conducting layer 6 may be a metal, for example, aluminum (Al).

As an example, the material of the third insulating layer 7 may be an organic material, for example, a resin.

As an example, the material of the source-drain electrically conducting layer 8 may be a metal, for example, chromium (Cr)/gold (Au) arranged in stack, wherein the thickness of the chromium is approximately 20±5 nm, and the thickness of the gold is approximately 40±5 nm.

As an example, the material of the fourth insulating layer 9 may be an inorganic material, for example, at least one of silicon nitride, silicon oxide and silicon oxynitride.

As an example, the material of the third electrically conducting layer 10 may be a metal, for example, gold (Au), the thickness of which is approximately 40±5 nm.

It should be noted that, in FIG. 2, the sensing electrodes 11B-1, 11B-2 are electrically connected by the second connecting electrode DJ2 and the first connecting electrode DJ1, both of the first connecting electrode DJ1 and the second grid Gate2 of the bigrid transistor are located at the second electrically conducting layer 6, and the first connecting electrode DJ1 and the second grid Gate2 of the bigrid transistor are connected by the lead located at the second electrically conducting layer 6. FIG. 2 does not illustrate the lead between the first connecting electrode DJ1 and the second grid Gate2 of the bigrid transistor.

In at least one embodiment of the present application, both of the first trace L1 and the second trace L2 are provided in the same layer as the sensing electrodes 11B-1, 11B-2.

In at least one embodiment of the present application, the first trace L1 and the second trace L2 may be provided at any one of the source-drain electrically conducting layer 8, the second electrically conducting layer 6 and the first electrically conducting layer 2.

Referring to FIG. 2, the third traces L3 described above (i.e., the leads for connecting the sensing electrodes and the first trace L1 or the leads for connecting the sensing electrodes and the second trace L2) may also be provided at the second electrically conducting layer 6.

In the detection base board according to the embodiments of the present application, as compared with an externally placed transistor, the transistor component is provided inside the film layers of the detection base board, which can reduce the resistance between the sensing electrodes and the second grid Gate2 of the bigrid transistor, reduces the connected externally placed leads, reduces the loss in the charge migration, and increases the detection sensitivity.

Taking the case as an example in which the protein marker is interleukin 20 (IL-20), it will be described below how to determine the concentration of the protein marker in the sample to be detected according to the variation value of the detection current, which particularly comprises:

Firstly, a reference standard variation curve of the variation value of the detection current with the variation of the concentration of interleukin 20 (IL-20) is determined, and the regression equation formula of the curve is obtained.

It will be described particularly below how to obtain the reference standard variation curve:

1: when the first grid Gate1 of the bigrid transistor controls the bigrid transistor to be turned on and the detected sample is not added, recording the initial electric-current value $I_0$ of the detecting unit 11; and introducing 1 pg·mL$^{-1}$ of IL-20 of into the detecting unit at the rate of 20 μL·min$^{-1}$ for 30 s, washing by using sulfuric acid of 0.005 nM, and measuring the detection current passing through the bigrid transistor under the response of 60 s.

2: when the first grid Gate1 of the bigrid transistor controls the bigrid transistor to be turned on and the detected sample is not added, recording the initial electric-current value Lo of the detecting unit 11; and introducing 2 pg·mL$^{-1}$ of IL-20 into the detecting unit at the rate of 20 μL·min$^{-1}$ for 30 s, washing by using sulfuric acid of 0.005 nM, and measuring the detection current passing through the bigrid transistor under the response of 60 s.

Figure 9:
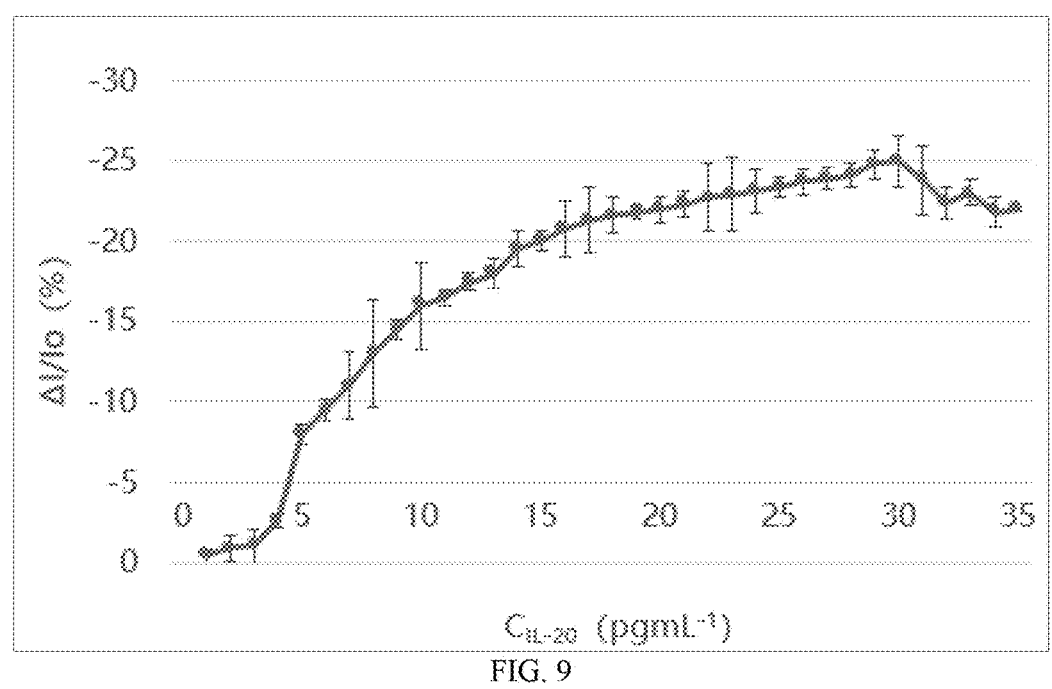
FIG. 9 is a curve of the variation value of the detection current of a detecting unit changing with the concentration of a protein marker according to an embodiment of the present application.

3: measuring sequentially the detection currents at 30 s after the IL-20 is introduced into the detecting unit at different concentration gradients (the step is similar to the preceding two steps), to obtain the variation curve of the detection current with the variation of the concentration of the interleukin 20 (IL-20) shown in FIG. 9; and fitting the curve, to obtain the regression equation formula $y = -0.5972 \ast x - 11.434$, where x represents the horizontal coordinate in FIG. 9, and y represents the vertical coordinate in FIG. 9.

In addition, it should be noted that it can be known according to the curve data in FIG. 9 that, in the range of 5-30 pg·mL$^{-1}$ of the interleukin 20 (IL-20), the regression equation formula has a high accuracy. When the concentration is less than 5 pg·mL$^{-1}$ and greater than 30 pg·mL$^{-1}$, the curve has a large fluctuation. Therefore, in the range of the actual measurement, when the concentration of the interleukin 20 (IL-20) exceeds the range of 5-30 pg·mL$^{-1}$, the detection result is not used as the practical reference basis.

Secondly, in the practical detection, by using the curve and/or the regression equation formula as a reference, according to the actual variation value of the detection current, the concentration of the interleukin 20 (IL-20) in the sample to be detected is calculated.

It should be noted that the methods of concentration calculation of other protein markers are similar to that of interleukin 20 (IL-20), and are not discussed further.

Figure 10:
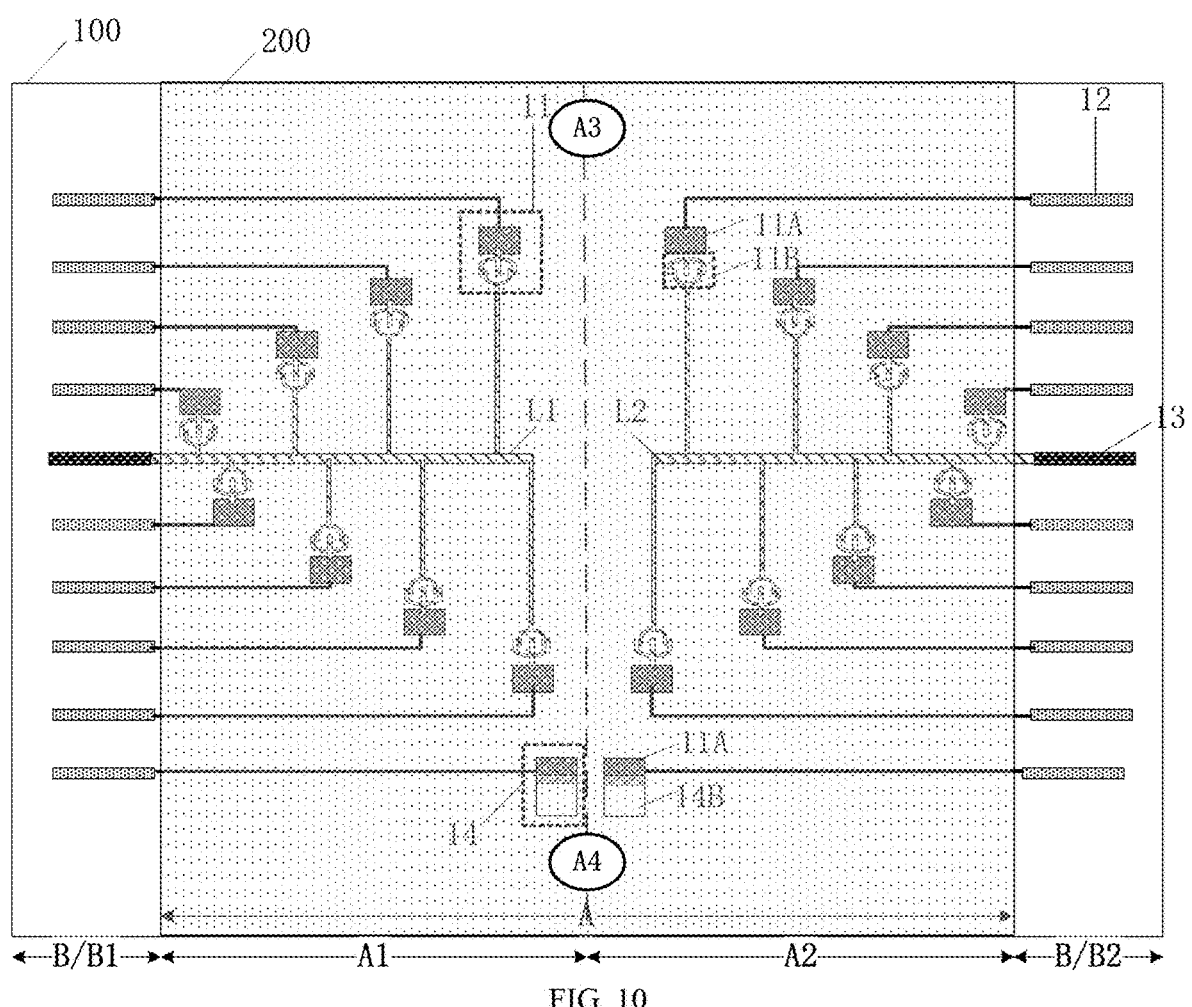
FIG. 10 is a schematic planar structural diagram of a detection chip according to an embodiment of the present application.

An embodiment of the present application provides a detection chip. As shown in FIG. 10, the detection chip comprises the detection base board stated above, and further comprises a cover plate 200 and an adhesive layer (not shown), the cover plate 200 covers the sample testing region A of the detection base board, the cover plate 200 is provided with a sample inputting hole (at the position of the label A3) and a sample outputting hole (at the position of the label A4), the adhesive layer is located between the detection base board and the cover plate 200, and the detection base board, the cover plate 200 and the adhesive layer form a cavity therebetween.

As an example, the material of the cover plate 200 may be a resin or a glass.

As an example, the material of the adhesive layer may be an adhesive or a glue.

In the practical fabricating process of the detection chip, the material of the adhesive layer is uniformly spread-coated onto the region of the sample testing region A of the detection base board close to the edge by using a glue dispenser, covered with the cover plate 200, baked at 100° C. for 5 min, and, after the temperature is increased under program controlling to 150° C., baked for approximately 10 min.

As an example, the thickness of the adhesive layer is 100 μm±10 μm, and the box thickness of the detection chip is substantially equal to the thickness of the adhesive layer.

In at least one embodiment of the present application, all of the detecting units 11 of the detection base board are located inside the same cavity.

In the chip according to the embodiments of the present application, as shown in FIG. 10, by configuring that the plurality of detecting units 11 are located inside the same cavity (not shown in FIG. 10), the different AML-relevant protein markers in the same sample to be detected can be identified simultaneously, to significantly increase the diagnosis accuracy, provide a high-efficiency clinical AML monitoring and detecting platform, and promote the development of individualized treatment. In addition, according to the coffee-ring effect of the solution, by configuring that, in the same sensing unit 11B, both of the outer contours of the two sensing electrodes (for example, the sensing electrode 11B-1 and the sensing electrode 11B-2 in FIG. 3 or FIG. 4) comprise an arc line, the contact area between the active ingredients in the sample to be detected and the sensing unit 11B can be increased, thereby increasing the detection sensitivity of the detecting units 11.

A method of detecting acute myelogenous leukemia by using the detection chip will be provided below, to examine the effect of detection by the detection chip according to the embodiments of the present application, which particularly comprises:

1: selecting 10 AML patients and 10 healthy subjects (all of the 10 AML patients and the 10 healthy subjects are voluntarily participating volunteers).

Figures 11, 12A, 12B, 12C:
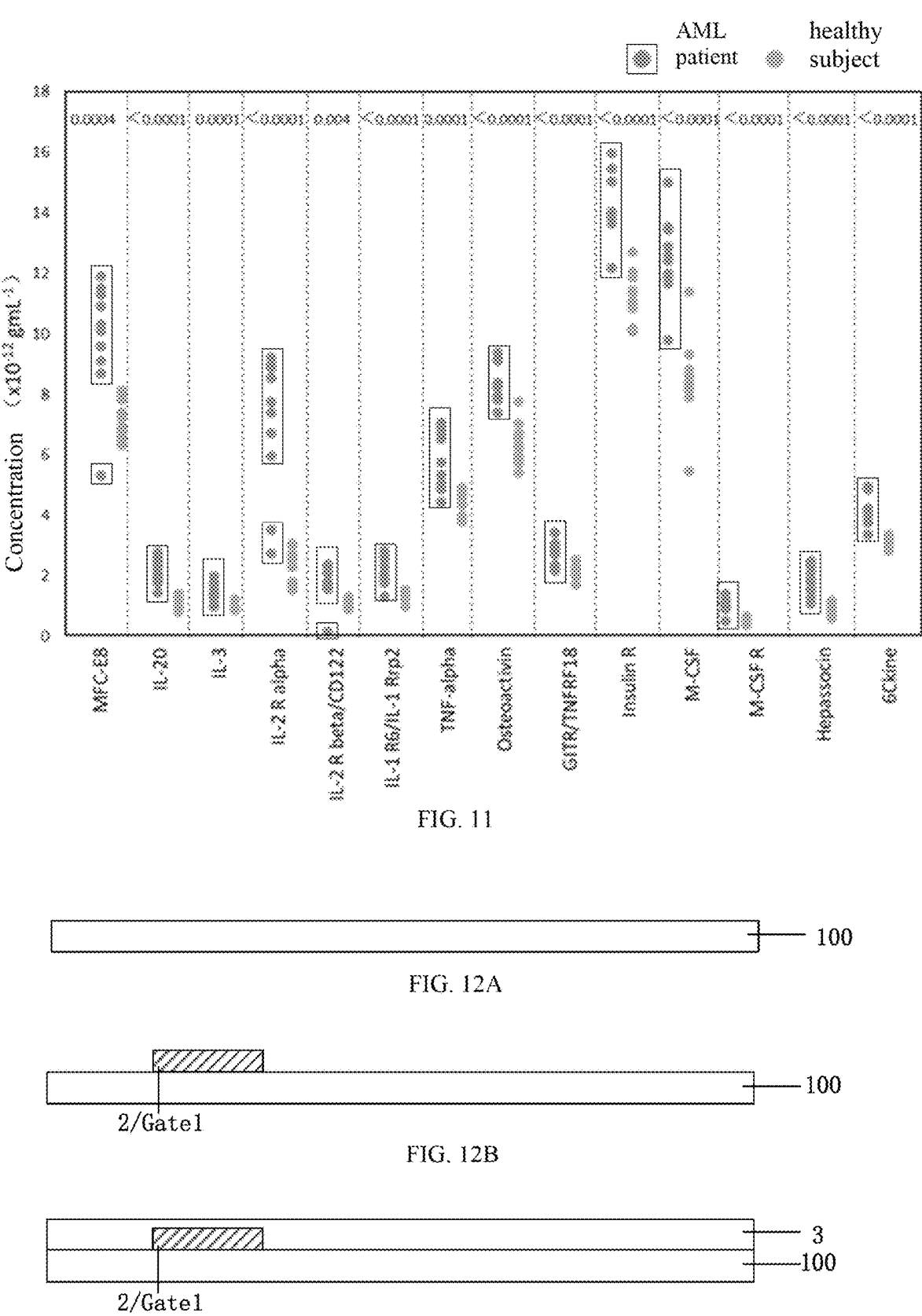
FIG. 11 is a scatter-plot distribution diagram of the detection results of a detection chip according to an embodiment of the present application.
FIGS. 12A-12L are diagrams of intermediate structures of a fabricating method of a detection chip according to an embodiment of the present application.

2: recording the initial electric-current value $I_0$, pretreating the blood samples of the 10 AML patients and the 10 healthy subjects, introducing the already treated serum samples into the detection chip at 20 μLmin$^{-1}$ for 30 s, washing by using sulfuric acid of 0.005 nM, measuring the state at 60 s of the current response, and, by using the linear range in the response curve that has been calibrated (i.e., the reference standard variation curve described above), calculating the concentrations of 14 protein markers, to obtain the diagram of the horizontal distribution of the concentrations of the protein markers in the 10 AML patients and the 10 healthy subjects shown in FIG. 11.

It can be seen from FIG. 7 that the concentrations of the multiple types of AML-relevant protein markers of the AML patients are basically greater than those of the healthy subjects. The multiple indicators do not only ensure the accuracy of the checkout results of the patients, thereby preventing false negative, but also ensure that false positive is not caused by misdiagnosis when a single indicator is used.

As compared with the diagnosis of the disease of the patient by measuring a single protein marker in the related art, because the detection chip according to the embodiments of the present application can specifically identify multiple types of AML-relevant protein markers simultaneously, the diagnosis accuracy is significantly increased. Even if detection abnormally happens in a certain individual single protein marker, the test results of the 14 AML-relevant protein markers can be comprehensively considered, to give a more accurate diagnosis result, thereby providing a high-efficiency clinical AML monitoring platform, and promoting the development of individualized treatment. In addition, the present application, as compared with conventional chips, highly increases the detection sensitivity, and, as a disposable consumable, has a lower fabrication cost, which prevents residual contamination.

An embodiment of the present application further provides a fabricating method of the detection chip, which particularly comprises:

1: providing the substrate 100 shown in FIG. 12A.

As an example, the material of the substrate 100 is a glass.

2: as shown in FIG. 12B, forming the first electrically conducting layer 2 on the substrate 100, wherein the first electrically conducting layer comprises the first grid Gate1 of the bigrid transistor.

Before the first electrically conducting layer 2 is formed, the substrate 100 is washed.

3: as shown in FIG. 12C, forming the first insulating layer 3.

Figures 12D, 12E, 12F, 12G, 12H, 12I:
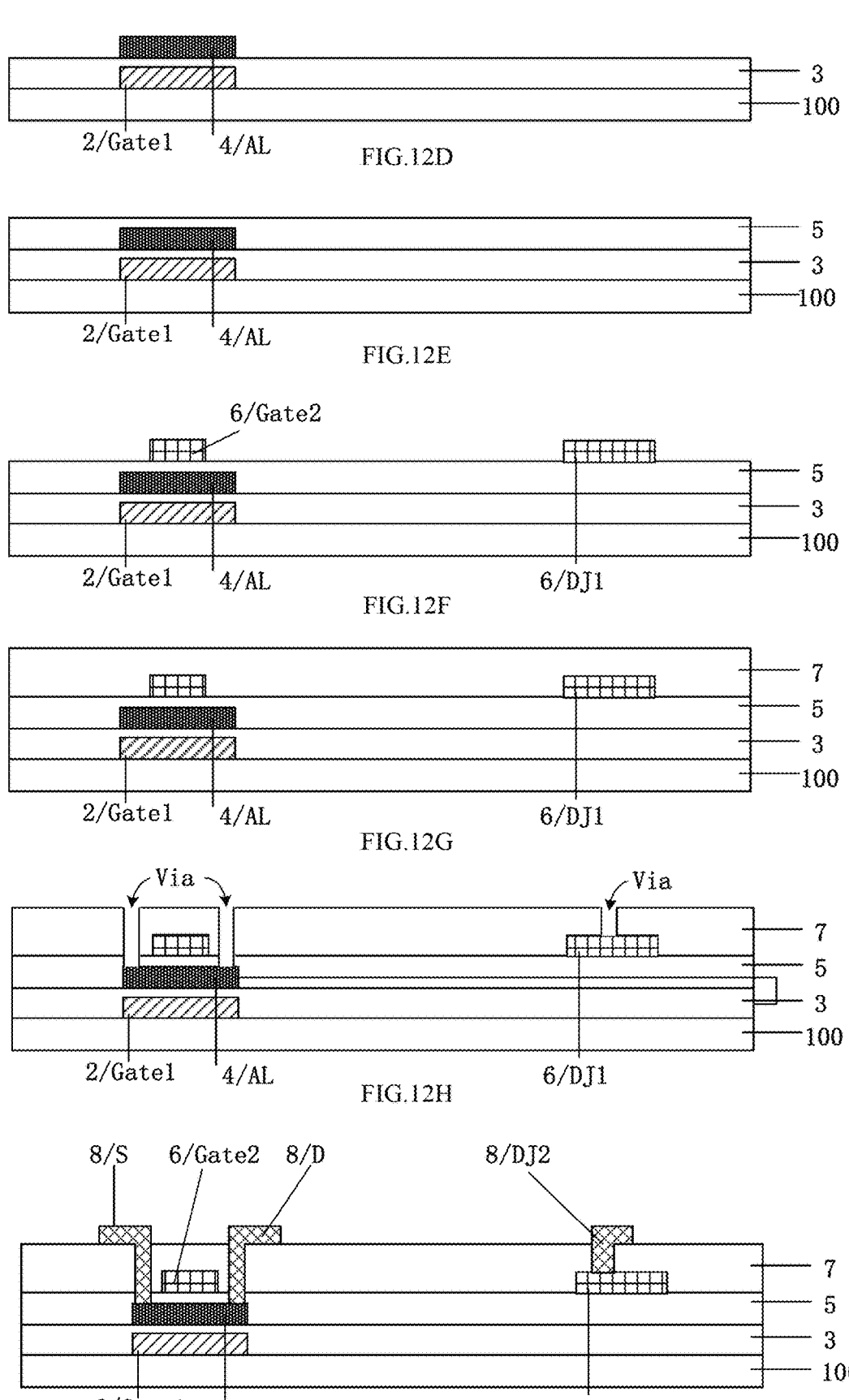

4: as shown in FIG. 12D, forming the semiconductor layer 4.

As an example, the thickness of the semiconductor layer 4 is 30 nm±5 nm.

The semiconductor layer 4 comprises the active part AL of the bigrid transistor, and the active part AL forms the channel region of the transistor, wherein the length L of the channel region is approximately 450±50 μm, and the width W of the channel region is approximately 500↑50 μm.

5: as shown in FIG. 12E, forming the second insulating layer 5.

6: as shown in FIG. 12F, forming the second electrically conducting layer 6, wherein the second electrically conducting layer 6 comprises the second grid Gate2 of the bigrid transistor.

7: as shown in FIG. 12G, forming the third insulating layer 7, and, by etching (for example, wet etching), forming the via hole Via shown in FIG. 12H.

8: as shown in FIG. 12I, forming the source-drain electrically conducting layer 8, wherein the source-drain electrically conducting layer 8 comprises the sources S and the drains D of the bigrid transistors and the plurality of second connecting electrodes DJ2.

Figure 12J:
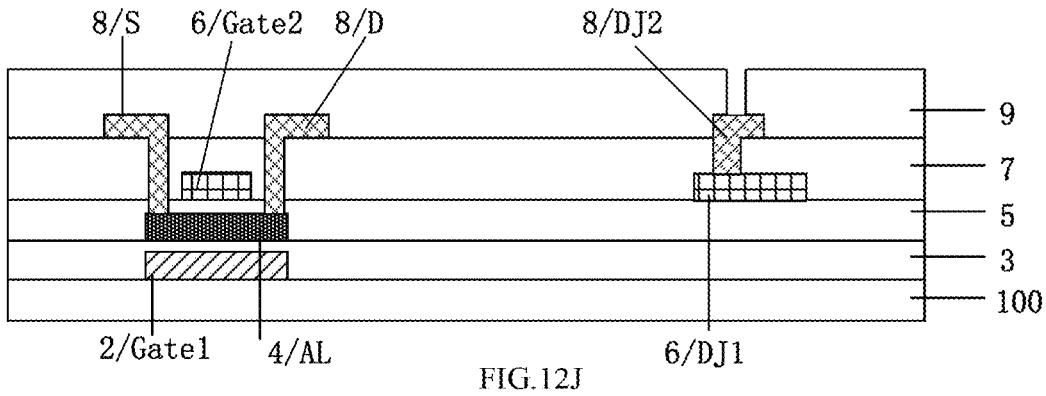

9: as shown in FIG. 12J, forming the fourth insulating layer 9, and, by etching (for example, wet etching), forming the via hole Via shown in FIG. 12J.

Figure 12K:
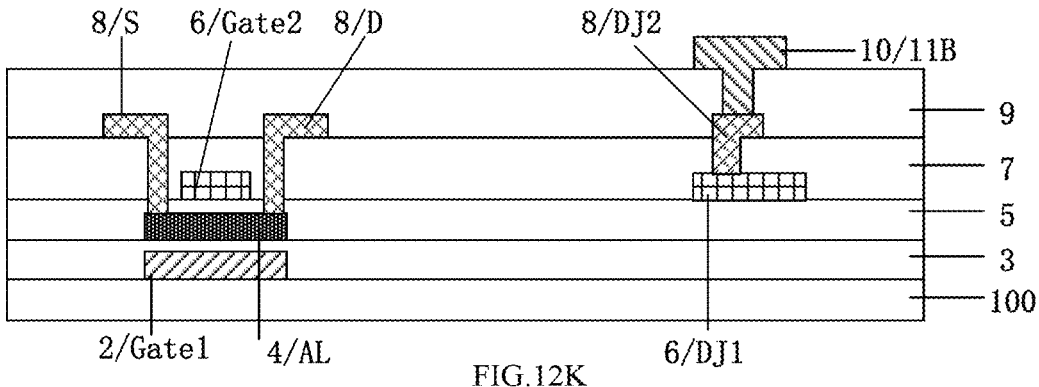

10: as shown in FIG. 12K, forming the third electrically conducting layer 10, wherein the third electrically conducting layer 10 comprises the sensing unit 11B (comprising the sensing electrode 11B-1 and the sensing electrode 11B-2).

Figure 12L:
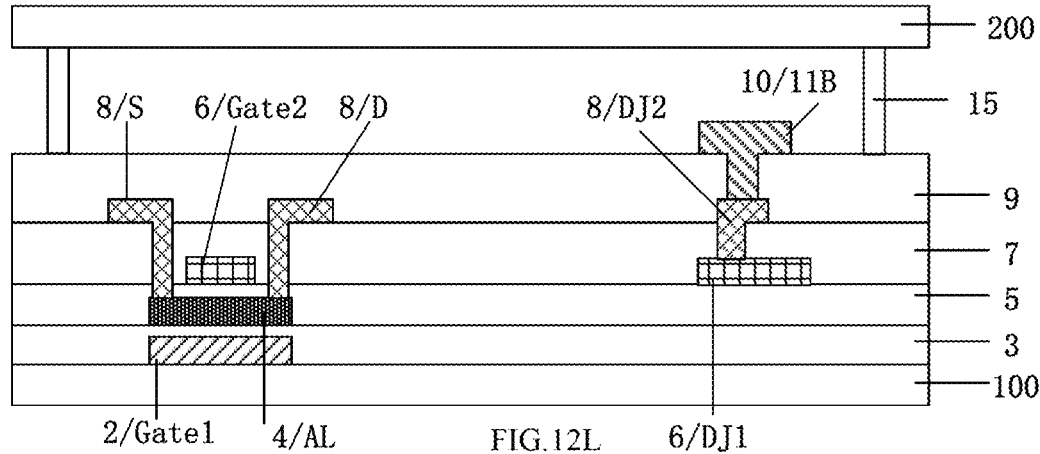

11: spread-coating the material of the adhesive layer 15 by adhesive dispensing, covering with the cover plate 200, baking at 100° C. for 5 min, and, after the temperature is increased under program controlling to 150° C., baking for approximately 10 min, to obtain the adhesive layer 15 and the cover plate 200 shown in FIG. 12L, wherein the detection base board, the cover plate 200 and the adhesive layer 15 form the cavity.

As an example, in the direction parallel to the plane where the substrate 100 is located, the planar pattern of the adhesive layer 15 is annular, and the width of the annular shape is approximately 1.2 mm±1 mm.

As an example, the size of the cover plate 200 is approximately 7 cm*2 cm*0.3 cm.

All of the detecting units 11 are located inside the same cavity. In order to simplify the figures, the figures according to the embodiments of the present application merely illustrate one detecting unit 11 inside the cavity, which is not a limitation on the quantity of the detecting units 11 inside the cavity.

The above are merely particular embodiments of the present application, and the protection scope of the present application is not limited thereto. All of the variations or substitutions that a person skilled in the art can easily envisage within the technical scope disclosed by the present application should fall within the protection scope of the present application. Therefore, the protection scope of the present application should be subject to the protection scope of the claims.

The invention claimed is:

1. A detection base board, wherein the detection base board comprises a substrate;

the substrate comprises a sample testing region;

the sample testing region comprises a plurality of detecting units, each of the detecting units comprises a sensing unit and a signal generating unit, and the sensing unit and the signal generating unit are electrically connected;

the sensing unit is configured to react with a sample to be detected and generate an electric signal, and the signal generating unit is configured to receive the electric signal and generate a detection current;

the sensing unit comprises a pair of sensing electrodes, and the pair of sensing electrodes are electrically connected to the signal generating unit; and contours of the sensing electrodes comprise an arc line;

wherein the signal generating unit comprises a bigrid transistor, and a first grid and a second grid of the bigrid transistor are configured to be connected to different electrically conducting components.

2. The detection base board according to claim 1, wherein each of the sensing electrodes comprises a plurality of extending parts and a connecting part connecting the extending parts;

in a same sensing electrode, the connecting part has a direction of extension intersecting with a direction of extension of the plurality of extending parts and connects all of the plurality of extending parts together, and the connecting part is located on a same side of the plurality of extending parts; and the sensing unit comprises a first sensing electrode and a second sensing electrode, a pattern of an orthographic projection on the substrate of the connecting part of the first sensing electrode and two extending parts connected to two ends of the connecting part is a first arch, a pattern of an orthographic projection on the substrate of the connecting part of the second sensing electrode and two extending parts connected to two ends of the connecting part is a second arch, and two ends of the first arch extend into a region enclosed by the second arch.

3. The detection base board according to claim 2, wherein a quantity of the extending parts of the first sensing electrode is at least two, a quantity of the extending parts of the second sensing electrode is at least three, and the extending parts of the first sensing electrode and the extending parts of the second sensing electrode are alternately arranged; and a shape of a pattern of an orthographic projection of each of the connecting parts on the substrate comprises an arc shape.

4. The detection base board according to claim 3, wherein a shape of a pattern of an orthographic projection of the first sensing electrode on the substrate is a U shape; and a shape of a pattern of an orthographic projection on the substrate of the connecting part of the second sensing electrode is an arc shape, and a shape of a pattern of an orthographic projection on the substrate of each of the extending parts of the second sensing electrode is a rectangle.

5. The detection base board according to claim 1, wherein the first grid of the bigrid transistor is electrically connected to a constant-voltage-signal inputting terminal, and the first grid is configured to control turning-on and turning-off of the bigrid transistor; and the second grid of the bigrid transistor is electrically connected to the pair of sensing electrodes, and the second grid is configured to control variation of an electric current in the bigrid transistor and simultaneously generating the detection current according to electric signals generated in the sensing electrodes.

6. The detection base board according to claim 5, wherein the substrate further comprises a signal-detection region located on at least one side of the sample-detection region, and the signal-detection region comprises at least one negative electrode terminal; and the negative electrode terminal is electrically connected to the second grid by the sensing electrodes.

7. The detection base board according to claim 6, wherein the negative electrode terminal is electrically connected to a correcting line, and the negative electrode terminal is configured to release electric charges inside the bigrid transistor to correct the bigrid transistor.

8. The detection base board according to claim 6, wherein the signal-detection region comprises a plurality of first signal acquiring terminals, the first signal acquiring terminals are electrically connected to the signal generating units, and a quantity of the first signal acquiring terminals is equal to a quantity of the signal generating units;

the signal-detection region further comprises a plurality of second signal acquiring terminals; and in each of the detecting units, a drain of the bigrid transistor is electrically connected to the first signal acquiring terminal, a source of the bigrid transistor is electrically connected to the second signal acquiring terminal; the first signal acquiring terminal, the drain of the bigrid transistor, the source of the bigrid transistor and the second signal acquiring terminal are configured to form an electrically conducting loop, and the detection current refers to an electric current in the loop within a detection time period.

9. The detection base board according to claim 6, wherein the sample testing region comprises at least one reference unit, and the reference unit comprises a reference electrode and the bigrid transistor; and in the reference unit, the first grid of the bigrid transistor is electrically connected to the constant-voltage-signal inputting terminal, the first grid is configured to control the turning-on and turning-off of the bigrid transistor, the second grid of the bigrid transistor is electrically connected to the reference electrode, a drain of the bigrid transistor is electrically connected to the first signal acquiring terminal, and a source of the bigrid transistor is electrically connected to the second signal acquiring terminal.

10. The detection base board according to claim 9, wherein the sample testing region comprises a first sub-region and a second sub-region;

the substrate comprises a first signal-detection sub-region and a second signal-detection sub-region that are located on two sides of the sample testing region;

each of the first sub-region and the second sub-region comprises eight detecting units;

within the first sub-region, four detecting units are arranged in a first direction, and the other four detecting units are arranged in a second direction, wherein the first direction and the second direction intersect;

the first direction and a direction from the first sub-region pointing to the second sub-region form an acute angle therebetween, and the second direction and the direction from the first sub-region pointing to the second sub-region form an acute angle therebetween; and arrangement of the detecting units within the second sub-region and arrangement of the detecting units within the first sub-region are symmetrical.

11. The detection base board according to claim 10, wherein the first sub-region comprises one first trace, the second sub-region comprises one second trace, and the first trace and the second trace have equal lengths and are arranged symmetrically;

both of the first trace and the second trace extend in the direction from the first sub-region pointing to the second sub-region; and the first trace is configured to connect the eight detecting units within the first sub-region together in series, and the second trace is configured to connect the eight detecting units within the second sub-region together in series.

12. The detection base board according to claim 11, wherein the first signal-detection sub-region is located on one side of the first sub-region away from the second sub-region, and the second signal-detection sub-region is located on one side of the second sub-region away from the first sub-region; and the first signal-detection sub-region comprises a first negative electrode terminal, the second signal-detection sub-region comprises a second negative electrode terminal, all of the second grids of all of the bigrid transistors within the first sub-region are electrically connected to the first negative electrode terminal by sequentially the sensing electrodes and the first trace, and all of the second grids of all of the bigrid transistors within the second sub-region are electrically connected to the second negative electrode terminal by sequentially the sensing electrodes and the second trace.

13. The detection base board according to claim 12, wherein the detection base board further comprises a plurality of third traces, and a direction of extension of the third traces intersects with the first trace;

some of the third traces are configured to connect the first trace and the detecting units within the first sub-region, and the other of the third traces are configured to connect the second trace and the detecting units within the second sub-region; and both of a range of lengths of traces connecting the detecting units and the first negative electrode terminal within the first sub-region and a range of lengths of traces connecting the detecting units and the second negative electrode terminal within the second sub-region are 0.5 cm-5 cm.

14. The detection base board according to claim 11, wherein the detection base board comprises a first electrically conducting layer, a first insulating layer, a semiconductor layer, a second insulating layer, a second electrically conducting layer, a third insulating layer, a source-drain electrically conducting layer, a fourth insulating layer and a third electrically conducting layer that are located on the substrate and are sequentially arranged;

the first electrically conducting layer comprises the first grids of the bigrid transistors, the semiconductor layer comprises active parts of the bigrid transistors, the second electrically conducting layer comprises the second grids of the bigrid transistors and a plurality of first connecting electrodes, and the source-drain electrically conducting layer comprises the sources and the drains of the bigrid transistors and a plurality of second connecting electrodes; and the sensing electrodes are electrically connected to the second grids of the bigrid transistors by sequentially the second connecting electrodes and the first connecting electrodes.

15. The detection base board according to claim 10, wherein within the first sub-region or the second sub-region, in a direction parallel to a plane where the substrate is located, a minimum distance between any two neighboring sensing units is greater than or equal to 1.2 cm.

16. A detection chip, wherein the detection chip comprises the detection base board according to claim 1, and further comprises a cover plate and an adhesive layer, the cover plate covers the sample testing region of the detection base board, the cover plate is provided with a sample inputting hole and a sample outputting hole, the adhesive layer is located between the detection base board and the cover plate, and the detection base board, the cover plate and the adhesive layer form a cavity therebetween; and all of the detecting units of the detection base board are located inside a same one instance of the cavity.

\* \* \* \* \*